US010393758B2

(12) United States Patent
Fernández Fernández et al.

(10) Patent No.: US 10,393,758 B2
(45) Date of Patent: Aug. 27, 2019

(54) METHODS FOR TREATING OR AMELIORATING MULTIPLE SCLEROSIS

(71) Applicants: SERVICIO ANDALUZ DE SALUD, Seville (ES); FUNDACIÓN PÚBLICA ANDALUZA PARA LA INVESTIGACIÓN DE MÁLAGA EN BIOMEDICINA Y SALUD (FIMABIS), Málaga (ES); UNIVERSIDAD DE MÁLAGA, Málaga (ES)

(72) Inventors: Óscar Fernández Fernández, Málaga (ES); Begoña Oliver Martos, Málaga (ES); Teresa Órpez Zafra, Málaga (ES); José Pavía Molina, Málaga (ES); Cristobalina Mayorga Mayorga, Málaga (ES); Laura Leyva Fernández, Málaga (ES); María Jesús Pinto Medel, Málaga (ES); Margarita Suardíaz García, Seville (ES)

(73) Assignee: UNIVERSIDAD DE MALAGA, Malaga (ES)

( * ) Notice: Subject to any disclaimer, the term of this patent is extended or adjusted under 35 U.S.C. 154(b) by 273 days.

(21) Appl. No.: 14/443,814

(22) PCT Filed: Nov. 22, 2013

(86) PCT No.: PCT/ES2013/070812
§ 371 (c)(1),
(2) Date: Sep. 25, 2015

(87) PCT Pub. No.: WO2014/080063
PCT Pub. Date: May 30, 2014

(65) Prior Publication Data
US 2016/0011212 A1   Jan. 14, 2016

(30) Foreign Application Priority Data
Nov. 22, 2012  (ES) .................................. 201231815

(51) Int. Cl.
*C07K 14/565*   (2006.01)
*C07K 14/705*   (2006.01)
*A61K 38/04*   (2006.01)
*G01N 33/68*   (2006.01)
*C07K 14/715*   (2006.01)
*G01N 33/564*   (2006.01)
*C07K 16/28*   (2006.01)
*A61K 38/00*   (2006.01)

(52) U.S. Cl.
CPC ....... *G01N 33/6896* (2013.01); *C07K 14/715* (2013.01); *C07K 14/7156* (2013.01); *C07K 16/2866* (2013.01); *G01N 33/564* (2013.01); *A61K 38/00* (2013.01); *G01N 2333/7156* (2013.01); *G01N 2800/285* (2013.01); *G01N 2800/52* (2013.01); *G01N 2800/56* (2013.01)

(58) Field of Classification Search
None
See application file for complete search history.

(56) References Cited

U.S. PATENT DOCUMENTS 5,821,078 A * 10/1998 Novick ................ C07K 14/715
435/252.3
2004/0018522 A1   1/2004 Dangond et al.

FOREIGN PATENT DOCUMENTS

EP         0679717 A2    11/1995
WO    WO-00/24417 A1    5/2000

OTHER PUBLICATIONS

Serena et al., (2008), J. of Neuroimmunology, vol. 197, pp. 54-62.*
Stadelmann et al., (2011), Biochimica et Biophysica Acta Vo. 1812, pp. 275-282.*
Paty et al., Neurology, vol. 43: pp. 662-667. (Year: 1993).*
Arduini, R. M. et al., "Characterization of a soluble ternary complex formed between human interferon-β-1a and its receptor chains," *Protein Science*, vol. 8, No. 9, pp. 1867-1877, 1999.
International Search Report for PCT/ES2013/070812 dated Mar. 5, 2014.
Lutfalla, G. et al., "Mutant U5A cells are complemented by an interferon-αβ receptor subunit generated by alternative processing of a new member of a cytokine receptor gene cluster," *The EMBO Journal*, vol. 14, No. 20, pp. 5100-5108, 1995.
Mealy, N. et al., "IFNAR-2," *Drugs of the Future*, vol. 29, No. 3, p. 292, 2004.
Novick, D. et al., "The Human Interferon α/β Receptor: Characterization and Molecular Cloning," *Cell*, vol. 77, No. 3, pp. 391-400, 1994.
Piehler, J. et al., "Biophysical Analysis of the Interaction of Human Ifnar2 Expressed in *E. coli* with IFNα2," *Journal of Molecular Biology*, vol. 289, No. 1, pp. 57-67, 1999.

* cited by examiner

*Primary Examiner* — Daniel E Kolker
*Assistant Examiner* — Jegatheesan Seharaseyon
(74) *Attorney, Agent, or Firm* — McCarter & English, LLP; Jill Ann Mello

(57) ABSTRACT

The invention relates to a recombinant protein and uses thereof in the diagnosis and treatment of multiple sclerosis. The invention also relates to the recombinant protein IFNAR2.3, antibodies, compositions comprising same, and uses thereof. Among the uses thereof, the invention especially relates to a method for the diagnosis of multiple sclerosis, and to the diagnosis kit. The invention further relates to the use of the protein IFNAR2.3 in the preparation of a medicament for the treatment of multiple sclerosis.

6 Claims, 22 Drawing Sheets
Specification includes a Sequence Listing.

```
1    ------------------------------ISYDSPDYTDESCTFKISLRNFRSILSWELKNHS   34   extracellular
1    ------------------------------ISYDSPDYTDESCTFKISLRNFRSILSWELKNHS   34   IFNAR2.3
1    MLLSQNAFIVRSLNLVLMVYISLVFGISYDSPDYTDESCTFKISLRNFRSILSWELKNHS       60   anti-IFNAR2rabbit
1    MLLSQNAFIVRSLNLVLMVYISLVFGISYDSPDYTDESCTFKISLRNFRSILSWELKNHS       60   anti-IFNAR2mouse
                                   ******************************

35   IVPTHYTLLYTIMSKPEDLKVVKNCANTTRSFCDLTDEWRSTHEAYVTVLEGFSGNTTLF       94   extracellular
35   IVPTHYTLLYTIMSKPEDLKVVKNCANTTRSFCDLTDEWRSTHEAYVTVLEGFSGNTTLF       94   IFNAR2.3
61   IVPTHYTLLYTIMSKPEDLKVVKNCANTTRSFCDLTDEWRSTHEAYVTVLEGFSGNTTLF       120  anti-IFNAR2rabbit
61   IVPTHYTLLYTIMSKPEDLKVVKNCANTTRSFCDLTDEWRSTHEAYVTVLEGFSGNTTLF       120  anti-IFNAR2mouse
     ************************************************************

95   SCSHNFWLAIDMSFEPPEFEIVGFTNHINVMVKFPSIVEEELQFDLSLVIEEQSEGIVKK       154  extracellular
95   SCSHNFWLAIDMSFEPPEFEIVGFTNHINVMVKFPSIVEEELQFDLSLVIEEQSEGIVKK       154  IFNAR2.3
121  SCSHNFWLAIDMSFEPPEFEIVGFTNHINVMVKFPSIVEEELQFDLSLVIEEQSEGIVKK       180  anti-IFNAR2rabbit
121  SCSHNFWLAIDMSFEPPEFEIVGFTNHINVMVKFPSIVEEELQFDLSLVIEEQSEGIVKK       180  anti-IFNAR2mouse
     ************************************************************

155  HKPEIKGNMSGNFTYIIDKLIPNTNYCVSVYLEHSDEQAVIKSPLKCTLLPPGQESESAE       214  extracellular
155  HKPEIKGNMSGNFTYIIDKLIPNTNYCVSVYLEHSDEQAVIKSPLKCTLLPPGQESEFS-       213  IFNAR2.3
181  HKPEIKGNMSGNFTYIIDKLIPNTNYCVSVYLEHSDEQAVIKSPLKCTLLPPGQESESAE       240  anti-IFNAR2rabbit
181  HKPEIKGNMSGNFTYIIDKLIPNTNYCVSVYLEHSDEQAVIKSPLKCTLLPPGQESESAE       240  anti-IFNAR2mouse
     *********************************************************

215  SAK---------------------------------------------------------     217  extracellular
214  ------------------------------------------------------------     213  IFNAR2.3
241  SAKIGGIITVFLIALVLTSTIVTLRWIGYICLRNSLPKVLRQGLTKGWNAVAIHRCSHNA     300  anti-IFNAR2rabbit
241  SAKIGGIITVFLIALVLTSTIVTLRWIGYICLRNSLPKVLRQGLTKGWNAVAIHRCSHNA     300  anti-IFNAR2mouse 218  --------------------------------   217   extracellular
214  --------------------------------   213   IFNAR2.3
301  LQSETPELKQSSCLSFPSSWDYKRASLCPSD    331   anti-IFNAR2rabbit
301  LQSETPELKQSSCLSFPSSWDYKRASLCPSD    331   anti-IFNAR2mouse
```

Fig. 13

METHODS FOR TREATING OR AMELIORATING MULTIPLE SCLEROSIS

RELATED APPLICATIONS

This application is a 35 U.S.C. § 371 national stage filing of International Application No. PCT/ES2013/070812, filed on Nov. 22, 2013, which claims priority to Spanish Patent Application No. P201231815, filed on Nov. 22, 2012. The entire contents of each of the foregoing applications are incorporated herein by reference.

SEQUENCE LISTING

The instant application contains a Sequence Listing which has been submitted electronically in ASCII format and is hereby incorporated by reference in its entirety. Said ASCII copy, created on Sep. 7, 2015, is named 125981-38101_SL.txt and is 12,147 bytes in size.

The present invention is within the field of biomedicine and biotechnology, and relates to the isolated soluble receptor IFNAR2.3, produced in a recombinant manner, and to use thereof in the preparation of a medicament for the prevention and/or treatment of an autoimmune demyelinating inflammatory disease, particularly multiple sclerosis, and for use thereof in the diagnosis of said diseases. It further relates to a method for the diagnosis of individuals with multiple sclerosis, to a kit and to uses thereof.

PRIOR ART

Multiple sclerosis (MS) is a chronic, presumably autoimmune, demyelinating inflammatory disease of the central nervous system (CNS). It is characterized by the presence of inflammatory lesions in the white and gray matter of the CNS, referred to as plaques, in which myelin loss and a certain degree of axonal degeneration occur.

Although various drugs have been developed in recent years to mitigate the effects of this disease, interferon beta (IFNβ) remains the most widely used treatment. Many clinical trials have demonstrated that interferon beta reduces outbreak frequency and severity, the number and volume of brain injuries observed by resonance and progression in the physical disability scale. However, a significant percentage of patients (30-50%) do not respond appropriately to treatment, since there continue to be outbreaks and progression in the physical disability scale.

IFNβ carries out its biological activity through interaction with the surface receptor IFNAR formed by two subunits, IFNAR1 and IFNAR2. After IFNβ binds to IFNAR2, dimerization of the two subunits and activation of the intracellular signaling cascade, the signal of which is transduced to the nucleus through the Jak-Stat pathway, occur. The antiviral, antiproliferative and immunomodulating activities of IFNβ are carried out in this manner.

The IFNAR2 subunit of the receptor undergoes an alternative mRNA processing which gives rise to three different isoforms: a short isoform (IFNAR2b), a long functionally active isoform (IFNAR2c) and a soluble isoform (sIFNAR2, IFNAR2.3 or IFNAR2a). Only IFNAR2c acts as a functional receptor together with IFNAR1 and is capable of mediating the biological effects of IFNβ. IFNAR2.3, which lacks cytoplasmic and transmembrane domains, has been identified in human biological fluids and although its role is not defined, it has been suggested to have the capacity for neutralizing the binding of IFNβ with the IFNAR2 receptor. It could therefore carry out modulating functions according to its concentration; on one hand, it could neutralize the binding of IFNβ to the IFNAR receptor or, in contrast, prolong the half-life of circulating IFNβ, preventing its degradation or oligomer formation. The function of the soluble IFNAR2 variant remains unknown today.

The clinical diagnosis of MS is complex. It is performed taking into consideration the existence of clinical criteria of spatial dissemination (the presence of symptoms and signs indicating the existence of two independent lesions in the CNS) and temporal dissemination (two or more episodes of neurological dysfunction).

Nerve conduction studies of the optic, sensory and motor nerves also provide evidence of the existence of the disease, since the demyelinating process involves a reduction in nerve signal conduction velocity. The study is conducted by comparing the reaction times with pre-established measurements.

The diagnosis process is completed by performing tests to exclude other diseases which can mimic sclerosis such as Devic's disease, sarcoidosis, vasculitis and Lyme disease.

Up until now, the paraclinical test par excellence for confirming the diagnosis of MS is the presence of oligoclonal bands (OCBs) in cerebrospinal fluid produced by cells located in the subarachnoid space which give rise to intrathecal IgG synthesis. The most sensitive method for detection thereof is polyacrylamide gel isoelectric focusing, which allows detecting OCB in up to 95% of MS cases. The main drawback of this technique is the need to perform a lumbar puncture on the patient, thus being a costly and invasive method for the patient.

Therefore, finding a paraclinical test that allows diagnosing individuals with MS in a manner that is much less invasive, bloodless and therefore, safer for the patient would be useful.

BRIEF DISCLOSURE OF THE INVENTION

A first aspect of the invention relates to a recombinant protein obtainable by a method which comprises:
a) integrating an insert with the nucleotide sequence SEQ ID NO. 1 in an expression vector,
b) transforming a host with the expression vector of step (a),
c) inducing the expression of the recombinant protein,
d) extracting the recombinant protein, and
e) optionally purifying the recombinant protein.

A second aspect of the invention relates to an antibody or a fragment thereof, specifically recognizing a recombinant protein according to the first aspect of the invention.

A third aspect of the invention relates to a composition comprising:
a) a protein comprising the amino acid sequence SEQ ID NO: 2,
b) the recombinant protein obtained according to the first aspect of the invention,
c) the protein sIFNAR2 (soluble IFNAR2 or IFANR2.3), or
d) the antibody according to the second aspect of the invention.

The composition is preferably a pharmaceutical composition, more preferably further comprises a pharmaceutically acceptable carrier and/or excipients. It can optionally comprise another active ingredient.

A fourth aspect of the invention relates to the composition of the third aspect of the invention for use thereof as a medicament.

A fifth aspect of the invention relates to the composition of the third aspect of the invention for the prevention, control, treatment and/or relief of an autoimmune demyelinating inflammatory disease, the autoimmune demyelinating inflammatory disease is preferably selected from the list consisting of: acute demyelinating diseases of the central nervous system and associated diseases (measles, chicken pox, rubella, enterovirus, Epstein-Barr, HTLV1, herpes type 6, herpes simplex and influenza A and B), acute transverse myelitis (TM), Devic's neuromyelitis optica, multiple sclerosis, optic neuritis, diffuse sclerosis or Schilder's disease, chronic relapsing polyneuropathy, leukodystrophy, Hughes syndrome, or any of the combinations thereof. More preferably, it relates to the composition of the third aspect of the invention for the prevention, control, treatment and/or relief of multiple sclerosis.

A sixth aspect of the invention relates to a method for obtaining useful data for the diagnosis of individuals with multiple sclerosis, which comprises:

a) obtaining an isolated biological sample from an individual, and b) detecting the expression product of IFNAR2.3, and optionally c) comparing the amounts obtained in step (b) with a reference amount.

A seventh aspect of the invention relates to a method for the diagnosis, prognosis and classification of individuals which comprises steps (a)-(c) according to the sixth aspect of the invention, and which further comprises assigning the individual of step (a) to the group of individuals with multiple sclerosis when they have a value greater than 2.14 above the cut-off point established in the ROC curve. In a preferred embodiment, it comprises assigning the individual of step (a) to the group of individuals without multiple sclerosis when they have a value less than 1.14 below the cut-off point established in the ROC curve.

An eighth aspect of the invention relates to a method for the prediction or prognosis of the progression of a patient, who has shown a clinically isolated syndrome (CIS), to multiple sclerosis which comprises steps (a)-(c) of the sixth aspect of the invention, and which further comprises assigning the individual of step (a) to the group of individuals who will progress to multiple sclerosis, when they have greater and significant levels with respect to a reference sample.

A ninth aspect of the invention relates to the composition of the third aspect of the invention for the prevention, control, treatment and/or relief of an individual of step (a) assigned to the group of individuals with multiple sclerosis or that progress to multiple sclerosis according to the seventh or eighth aspect of the invention.

A tenth aspect of the invention relates to a kit or device comprising the elements necessary for quantifying the expression product of IFNAR2.3, preferably the recombinant protein according to the first aspect of the invention.

An eleventh aspect of the invention relates to the use of the kit according to the tenth aspect of the invention for carrying out a method as described in the sixth, seventh or eighth aspect of the invention.

A twelfth aspect of the invention relates to a computer-readable storage medium comprising programming instructions capable of making a computer carry out the steps of the method according to the sixth, seventh or eighth aspect of the invention.

A last aspect of the invention relates to a transmissible signal comprising programming instructions capable of making a computer carry out the steps of the method according to the sixth, seventh or eighth aspect of the invention.

DISCLOSURE OF THE INVENTION

The authors of the present invention have developed a method to aid in the diagnosis of multiple sclerosis and designed a semi-quantitative sandwich ELISA for determining serum IFNAR2.3 in serum. To validate this assay, the authors have cloned and purified the protein IFNAR2.3, such that it can serve as a positive control to be included in the assay. Each step of the technique has been optimized and the intra-assay and inter-assay variation thereof has been calculated. Once the methodology has been developed and optimized, the values of soluble IFNAR2 in the serum of MS patients and healthy controls were determined. Furthermore, the authors of the invention have proven, in an animal model for MS (animal model of experimental allergic encephalitis or EAE), that the soluble IFNAR2 (IFNAR2.3 or sIFNAR2) is effective both in the prevention and treatment of MS.

Recombinant Protein of the Invention

The authors of the invention have cloned and purified the protein IFNAR2.3. Furthermore, by means of the cloning method used, they have added a histidine-asparagine tag at the carboxyl-terminal end, being fused to the recombinant protein like a label. After producing the recombinant protein in the host cell, the cell lysate is passed through an affinity column for purification. The fusion protein with the label is retained in the column whereas the other proteins and other contaminants flow through the column.

Therefore, a first aspect of the invention relates to a recombinant protein obtainable by a method which comprises:

a) integrating an insert with the nucleotide sequence SEQ ID NO. 1 in a gene construct or an expression vector, b) transforming a host with the expression vector of step (a), c) inducing the expression of the recombinant protein, d) extracting the recombinant protein, and e) purifying the recombinant protein The design of the vector based on genetic engineering techniques and the selection of the host cell greatly determine the characteristics of the recombinant protein.

The gene construct of the invention can comprise, in addition to the nucleotide sequence SEQ ID NO. 1, elements regulating the expression of said sequence. Said regulatory elements include promoters and enhancers. Promoters are typically positioned in position 5' with respect to the transcription or translation start site. Enhancers are capable of influencing gene expression when they are located in position 5' or 3' with respect to the cDNA or when they are part of an intron. Regulatory sequences include, in addition to promoters, sequences facilitating translation, processing signals for introns, stop codons, signal sequences, internal ribosome entry site (IRES) and polyadenylation signals.

The expression vector comprising the nucleotide sequence SEQ ID NO. 1 or a gene construct of the invention is operatively coupled with a sequence regulating the expression of said nucleotide sequence SEQ ID NO. 1 or of said gene construct. The person skilled in the art will find that the type of vector suitable for the expression of nucleic acids and gene constructs of the invention, will depend on the organism in which the polynucleotide of the invention is to be expressed.

In a preferred embodiment of this aspect of the invention, the expression vector is the prelinearized vector pEcoli-Cterm 6xHN Linear.

A host cell or organism can comprise the gene construct of the invention or a vector, as defined in the invention. In principle, any type of host organism known to the person skilled in the art can be used in the present invention, such as a bacterial strain (*Escherichia coli*, *Bacillus subtilis* and the like), a yeast strain (*Saccharomyces cerevisiae*, *Pichia pastoris*, *Kluyveromyces lactis*, *Hansenula polymorpha* and the like), a transgenic plant (dicotyledons or monocotyledons), an insect cell, for example, baculovirus, a mammal cell (COS cells, CHO cells, C127 cells, HeLa cells and the like) and a non-human transgenic organism (for example, a mouse, a cow, a goat, a rabbit, a pig, etc.).

In another preferred embodiment of this aspect of the invention, the host of step (b) are expression bacteria. More preferably, the expression bacteria are BL21(DE3). The BL21(DE3) expression bacteria are chemically competent *Escherichia coli* cells having a suitable genotype for transformation and protein expression, and the genome of which is known (Genome sequences of *Escherichia coli* B strains REL606 and BL21(DE3). Jeong H, et al. J Mol Biol 2009 Dec. 11).

A competent bacterium is characterized by having a weakened bacterial wall and it is therefore easier for it to capture a foreign DNA by means of an electric or heat shock process (transformation). Expression bacteria are used to produce the protein. In this specification, expression bacteria are those having the necessary machinery to overexpress the inserted cDNA and produce the recombinant protein.

In another preferred embodiment, the integration of the nucleotide sequence SEQ ID NO: 1 of step (a) is performed by means of a ligation process.

To perform the ligation process, the insert mixture: plasmid was resuspended in the product In-Fusion Dry-Down pellet (Clontech). In-Fusion Dry-Down pellet is a lyophilisate containing the In-Fusion enzyme which favors the binding of the insert to the plasmid as a result of the homology in the nucleotide sequence present in both.

Therefore, in another preferred embodiment of the invention a lyophilisate comprising the In-Fusion enzyme is used in the ligation. This enzyme is a poxvirus DNA polymerase with 3'-5' exonuclease activity, which is capable of binding single-stranded DNA molecules having short homologous sequences at the ends thereof, such as an amplified PCR product and a vector.

In another preferred embodiment, the insert is synthesized using primers having nucleotide sequences SEQ ID NO: 5 and SEQ ID NO: 6.

Another aspect relates to a protein comprising the amino acid sequence SEQ ID NO: 2, or to the recombinant protein of the invention (soluble IFNAR2, sIFNAR2 or IFNAR2.3), or the protein of the invention (soluble IFNAR2, sIFNAR2 or IFNAR2.3) obtained by other non-recombinant means, for use thereof as a medicament; or, alternatively, to the use of a protein comprising the amino acid sequence SEQ ID NO: 2 or to the recombinant protein of the invention, or the protein of the invention (soluble IFNAR2, sIFNAR2 or IFNAR2.3) obtained by other non-recombinant means, in the preparation of a medicament. Although the protein of the invention (soluble IFNAR2, sIFNAR2 or IFNAR2.3) is preferably a recombinant protein, and even more preferably a recombinant protein obtained by the method described in the present invention, since the described methods for obtaining and purifying same are advantageous, it can be obtained by any method known in the state of the art for obtaining proteins.

Another aspect relates to a protein comprising the amino acid sequence SEQ ID NO: 2, the recombinant protein of the invention (soluble IFNAR2, sIFNAR2 or IFNAR2.3), or the protein of the invention (soluble IFNAR2, sIFNAR2 or IFNAR2.3) obtained by other non-recombinant means, for use thereof in the prevention, control, treatment and/or relief of an autoimmune demyelinating inflammatory disease, or alternatively, to the use of a protein comprising the amino acid sequence SEQ ID NO: 2, or to the recombinant protein of the invention (soluble IFNAR2, sIFNAR2 or IFNAR2.3), or the protein of the invention (soluble IFNAR2, sIFNAR2 or IFNAR2.3) obtained by other non-recombinant means, in the preparation of a medicament for the diagnosis, prevention, control, treatment and/or relief of an autoimmune demyelinating inflammatory disease.

In another more preferred embodiment, the autoimmune demyelinating inflammatory disease is selected from the list consisting of: acute demyelinating diseases of the central nervous system and associated diseases (measles, chicken pox, rubella, enterovirus, Epstein-Barr, HTLV1, herpes type 6, herpes simplex and influenza A and B), acute transverse myelitis (TM), Devic's neuromyelitis optica, multiple sclerosis, optic neuritis, diffuse sclerosis or Schilder's disease, chronic relapsing polyneuropathy, leukodystrophy, Hughes syndrome, or any of the combinations thereof. Still more preferably, the inflammatory demyelinating disease is multiple sclerosis.

Another aspect relates to a protein comprising the amino acid sequence SEQ ID NO: 2, the recombinant protein of the invention (soluble IFNAR2, sIFNAR2 or IFNAR2.3), or the protein of the invention (soluble IFNAR2, sIFNAR2 or IFNAR2.3) obtained by other non-recombinant means, for use thereof in the diagnosis of multiple sclerosis, and more preferably, in the differential diagnosis of multiple sclerosis.

Antibodies and Compositions of the Invention and Uses Thereof

As demonstrated in the examples of the invention, the recombinant protein of the invention, and/or the protein sIFNAR2, can be used for the prevention and treatment of autoimmune demyelinating inflammatory diseases such as multiple sclerosis. Furthermore, the antibodies or fragments thereof capable of binding to the recombinant protein of the invention are also an object of the present invention. These antibodies or fragments thereof can be readily obtained from antisera.

The antisera for the recombinant protein described in the present invention can be generated by standard techniques, for example, by injecting the recombinant protein of the invention in a suitable animal and collecting and purifying the antisera of the animals. The antibodies or fragments thereof that bind to SEQ ID NO: 2, or a variant sequence thereof according to the invention, can be identified by standard immunoassays. The antibodies thus obtained (hereinafter, antibodies of the invention) can be used for the method of diagnosis of the invention. The antibodies or fragments thereof are preferably monoclonal antibodies.

Another aspect the invention therefore relates to an antibody or a fragment thereof specifically recognizing the recombinant protein of the invention, hereinafter antibody of the invention. Antibodies contemplated in the context of the present invention include polyclonal antisera, purified IgG molecules, supernatants or ascitic fluid containing monoclonal antibodies, Fv, Fab, Fab' and F(ab')$_2$ fragments, ScFv diabodies, triabodies, tetrabodies and humanized antibodies.

In another aspect, the invention relates to a composition, hereinafter composition of the invention, comprising:
  a) a protein comprising the amino acid sequence SEQ ID NO: 2,
  b) the recombinant protein of the invention,
  c) the protein of the invention (soluble IFNAR2, sIFNAR2 or IFNAR2.3) obtained by other non-recombinant means, and/or d) the antibody of the invention or a fragment thereof.

Said composition can be a pharmaceutical composition. Another aspect of the invention therefore relates to pharmaceutical compositions, hereinafter pharmaceutical compositions of the invention, comprising at least one of the polynucleotides of the invention, polypeptides of the invention or the mature form thereof, an antibody of the invention or a fragment thereof, the recombinant protein of the invention, the protein of the invention (soluble IFNAR2, sIFNAR2 or IFNAR2.3) obtained by other non-recombinant means, and/or accompanied by a pharmaceutically acceptable excipient. For use in medicine, the compounds and combinations of compounds of the invention can be formulated together with an excipient which is acceptable from the pharmaceutical viewpoint. Preferred excipients for use in the present invention include sugars, starches, celluloses, gums, proteins and others. In a particular embodiment, the pharmaceutical composition of the invention will be formulated in a solid pharmaceutical dosage form (e.g., tablets, capsules, dragées, granules, suppositories, etc.) or a liquid pharmaceutical dosage form (e.g., solutions, suspensions, emulsions, etc.), but without being limited thereto. In another particular embodiment, the pharmaceutical compositions of the invention can be administered by any route, including, without limitation, oral, intravenous, intramuscular, intra-arterial, intramedullary, intrathecal, intraventricular, transdermal, subcutaneous, intraperitoneal, intranasal, enteral, topical, sublingual or rectal route.

Another aspect of the invention relates to the composition of the invention or the pharmaceutical composition of the invention for use thereof as a medicament, or alternatively, to the use of the composition of the invention or the pharmaceutical composition of the invention in the preparation of a medicament.

As it is used herein, the term "medicament" refers to any substance used for the prevention, diagnosis, relief, treatment or cure of diseases or the prevention of undesired physiological states in humans and animals.

Another aspect relates to the composition of the invention or to the pharmaceutical composition of the invention for use thereof in the prevention, control, treatment and/or relief of an autoimmune demyelinating inflammatory disease, or alternatively, to the use of the composition of the invention or of the pharmaceutical composition of the invention in the preparation of a medicament for the prevention, control, treatment and/or relief of an autoimmune demyelinating inflammatory disease.

In another more preferred embodiment, the autoimmune demyelinating inflammatory disease is selected from the list consisting of: acute demyelinating diseases of the central nervous system and associated diseases (measles, chicken pox, rubella, enterovirus, Epstein-Barr, HTLV1, herpes type 6, herpes simplex and influenza A and B), acute transverse myelitis (TM), Devic's neuromyelitis optica, multiple sclerosis, optic neuritis, diffuse sclerosis or Schilder's disease, chronic relapsing polyneuropathy, leukodystrophy, Hughes syndrome, or any of the combinations thereof. Still more preferably, the inflammatory demyelinating disease is multiple sclerosis.

Method of Diagnosis of the Invention

The authors of the invention have found that the discriminating capacity of the detection of IFNAR2.3 in serum alone, between MS patients and controls, is high taking into account that the case at hand relates to a univariate indicator, and have developed an ELISA technique for detecting soluble IFNAR2 in serum, that serves as a paraclinical test for the diagnosis of MS. It is a technique that is much less invasive for the patient and less costly compared to oligoclonal bands, and could be used as a prior screening method, such that the oligoclonal bands would only need to be performed in the case of patients who obtain ELISA values that may give rise to doubt. To that end, after normalizing the absorbance data and establishing a cut-off point to distinguish between positive and negative results, a ROC curve with an area under the curve of 0.820 has been obtained, and different cut-off points which will provide different sensitivity and specificity according to the requirements the test calls for have been established.

Another aspect of the invention therefore relates to the use of IFNAR2.3 for the diagnosis of individuals with multiple sclerosis.

Another aspect of the invention relates to a method for obtaining useful data, hereinafter first method of the invention, for the diagnosis of individuals with multiple sclerosis, which comprises:

a) obtaining an isolated biological sample from an individual, and b) detecting the expression product of IFNAR2.3.

In another preferred embodiment, the first method of the invention further comprises:

c) comparing the expression product of IFNAR2.3 obtained in step (b) with a reference amount.

The reference amount is obtained from IFNAR2.3 constitutive expression values in a group of healthy individuals or, alternatively, individuals who do not have multiple sclerosis. Suitable reference amounts can be determined by the method of the present invention from a reference sample which can be analyzed, for example, simultaneously or consecutively, together with the biological test sample. Therefore, the reference sample can be, for example, but not being limited to, negative controls, i.e., the amounts detected by the method of the invention in samples of individuals who do not suffer the disease that is to be diagnosed. The expression product of IFNAR2.3 of step (b) of the first method of the invention is preferably the protein IFNAR2.3. In another more preferred embodiment, step (c) of the invention comprises comparing the detection of the protein IFNAR2.3 in the biological sample of (a) with the detection of the protein IFNAR2.3 in a reference population.

Steps (b) and/or (c) of the methods described above can be completely or partially automated, for example, by means of a robotic sensing equipment for the detection of the amount in step (b) or the computerized comparison in step (c).

The method of the invention is an in vitro method, and the sample on which the parameters are measured is an isolated sample. Therefore, an "isolated biological sample" includes, but is not limited to, cells, tissues and/or biological fluids of an organism, obtained by means of any method known by a person skilled in the art. The isolated biological sample from an individual of step (a) is preferably serum. In another preferred embodiment, the isolated biological sample from an individual of step (a) is cerebrospinal fluid.

As it is used herein, the term "individual" refers to animals, preferably mammals, and more preferably, humans. The term "individual" does not seek to be limiting in any aspect, the individual being able to be of any age, sex and in any physical condition.

The detection of the expression product of IFNAR2.3 can be performed by any means known in the state of the art.

Although the measurement of the expression product of IFNAR2.3 can be qualitative, the amount or concentration of said expression product can also preferably be determined in a semi-quantitative or quantitative manner and can be carried out directly or indirectly. Direct measurement refers to the measurement of the amount or concentration of the expression product of the genes based on a signal which is obtained directly from protein detection. Said signal—which can also be referred to as intensity signal—can be obtained, for example, by measuring an intensity value of a chemical or physical property of said products. Indirect measurement includes the measurement obtained from a secondary component or a biological measurement system (for example, the measurement of cell responses, ligands, "labels" or enzymatic reaction products).

As it is used herein, the term "amount" refers, but is not limited to, the absolute or relative amount of the expression products of the genes or of the antibodies, as well as to any other value or parameter related thereto or that can be derived therefrom. Said values or parameters comprise signal intensity values obtained from any of the physical or chemical properties of said expression products obtained by means of direct measurement. Additionally, said values or parameters include all those obtained by means of indirect measurement, for example, any of the measurement systems described elsewhere herein.

As it is used herein, the term "comparison" refers, but is not limited to, comparison of the expression products of IFNAR2.3 in a test sample with respect to the reference population, or alternatively, comparison of the amount of the expression products of the genes or the amount of antibodies against IFNAR2.3 of the biological sample to be analyzed, also referred to as biological test sample, with an amount of the expression products of the genes or with an amount of antibodies against IFNAR2.3 of one or more desirable reference samples. The reference sample can be analyzed, for example, simultaneously or consecutively, together with the biological test sample. The comparison described in section (c) of the method of the present invention can be performed manually or computer-aided.

Type I interferons (alpha, beta and omega) carry our their action through interaction with the membrane receptor IFNAR formed by two subunits, IFNAR1 and IFNAR2. The IFNAR2 subunit of the receptor undergoes an alternative mRNA processing which gives rise to three different forms: a short form (IFNAR2b), a long functionally active form (IFNAR2c) and a soluble form (sIFNAR2, IFNAR2.3 or IFNAR2a). Only IFNAR2c acts as a functional receptor together with IFNAR1 and is capable of mediating the biological effects of IFNβ through the activation of JAK-STAT signaling cascade.

Many transcription variants at least encoding two different isoforms have been found for this gene. The amino acid sequence of IFNAR2.3 has a GenBank (NCBI) accession number of L41943.1 and is found in SEQ ID NO: 2. Said SEQ ID NO: 2 is represented by the following amino acid sequence:

(MLLSQNAFIFRSLNLVLMVYISLVFGISYDSPDYTDESCTFKISLRNFR

SILSWELKNHSIVPTHYTLLYTIMSKPEDLKVVKNCANTTRSFCDLTDEW

RSTHEAYVTVLEGFSGNTTLFSCSHNFWLAIDMSFEPPEFEIVGFTNHIN

VMVKFPSIVEEELQFDLSLVIEEQSEGIVKKHKPEIKGNMSGNFTYIIDK

LIPNTNYCVSVYLEHSDEQAVIKSPLKCTLLPPGQESEFS).

In the context of the present invention, IFNAR2.3 is also defined by a polynucleotide or nucleotide sequence which is the coding sequence of the protein in SEQ ID NO: 2, and would comprise different variants originating from:

a) nucleic acid molecules encoding a polypeptide comprising the amino acid sequence of SEQ ID NO: 2, b) nucleic acid molecules the complementary strand of which hybridizes with the polynucleotide sequence of a), c) nucleic acid molecules the sequence of which differs from a) and/or b) due to genetic code degeneracy, d) nucleic acid molecules encoding a polypeptide comprising the amino acid sequence with an identity of at least one 60%, 70%, 80%, 90%, 95%, 98% or 99% with SEQ ID NO: 2, and in which the polypeptide encoded by said nucleic acids has the activity and structural characteristics of the protein IFNAR2.3. The molecule in GenBank (NCBI) sequence L41943.1 and SEQ ID NO: 1 is included among said nucleic acid molecules. Said SEQ ID NO: 1 is represented by the following nucleotide sequence:

(agatgtaaaagtcaagagaagactctaaaaatagcaaagatgcttttga gccagaatgccttcatcttcagatcacttaatttggttctcatggtgtat atcagcctcgtgtttggtatttcatatgattcgcctgattacagatga atcttgcactttcaagatatcattgcgaaatttccggtccatcttatcat gggaattaaaaaaccactccattgtaccaactcactatacattgctgtat acaatcatgagtaaaccagaagatttgaaggtggttaagaactgtgcaaa taccacaagatcattttgtgacctcacagatgagtggagaagcacacacg aggcctatgtcaccgtcctagaaggattcagcgggaacacaacgttgttc agttgctcacacaatttctggctggccatagacatgtcttttgaaccacc agagtttgagattgttggttttaccaaccacattaatgtgatggtgaaat ttccatctattgttgaggaagaattacagtttgatttatctctcgtcatt gaagaacagtcagagggaattgttaagaagcataaacccgaaataaaagg aaacatgagtggaaatttcacctatatcattgacaagttaattccaaaca cgaactactgtgtatctgtttatttagagcacagtgatgagcaagcagta ataaagtctcccttaaaatgcaccctccttccacctggccaggaatcaga attttcataactttttagcctggccatttcctaacctgccaccgttggaa gccatggatatggtggaggtcatttacatcaacagaaagaagaaagtgtg ggattataattatgatgatgaaagtgatagcgatactgaggcagcgccca ggacaagtggcggtggctataccatgcatggactgactgtcaggcctctg ggtcaggcctctgccacctctacagaatcccagttgatagaccggagtc cgaggaggagcctgacctgcctgaggttgatgtggagctccccacgatgc caaaggacagccctcagcagttggaactcttgagtgggcctgtgagagg agaaagagtccactccaggaccctttccccgaagaggactacagctccac ggaggggtctgggggcagaattaccttcaatgtggacttaaactctgtgt ttttgagagttcttgatgacgaggacagtgacgacttagaagcccctctg atgctatcgtctcatctgtgaagagatggttgacccagaggatcctgataa tgtgcaatcaaaccatttgctggccagcggggaagggacacagccaacct ttcccagccctcttcagagggcctgtggtccgaagatgctccatctgat caaagtgacacttctgagtcagatgttgaccttggggatggttatataat gagatgactccaaaactattgaatgaacttggacagacaagcacctacag ggttctttgtctctgcatcctaacttgctgccttatcgtctgcaagtgtt -continued

```
ctccaagggaaggaggaggaaactgtggtgttcctttcttccaggtgaca tcacctatgcacattcccagtatggggaccatagtatcattcagtgcatt gtttacatattcaaagtggtgcactttgaaggaagcacatgtgcacctt cctttacactaatgcacttaggatgtttctgcatcatgtctaccagggag cagggttccccacagtttcagaggtggtccaggaccctatgatatttctc ttctttcgttctttttttttttttttttgagacagagtctcgttctgtcgc ccaagctggagcgcaatggtgtgatcttggctcactgcaacatccgcctc ccgggttcaggtgattctcctgcctcagcctcccctcgcaagtagctggga ttacaggcgcctgccaccatgcctagcaaattttgtattttagtggag acaggattttaccatgttggccaggctggtctcgaactcctgacctcaag tgatctgccctcctcagcctcgtaaagtgctgggattacaggggtgagcc gctgtgcctggctggccctgtgatatttctgtgaaataaattgggccagg gtgggagcagggaaagaaaaggaaaatagtagcaagagctgcaaagcagg caggaagggaggaggagagccaggtgagcagtggagagaaggggggccct gcacaaggaaacagggaagagccatcgaagtttcagtcggtgagccttgg gcacctcacccatgtcacatcctgtctcctgcaattggaattccaccttg tccagccctccccagttaaagtggggaagacagactttaggatcacgtgt gtgactaatacagaaaggaaacatggcgtcggggagagggataaaacctg aatgccatattttaagttaaaaaaaaaaaa).
```

In another preferred embodiment, the detection of the amount of expression product of IFNAR2.3 is performed by means of an immunoassay. As it is used herein, the term "immunoassay" refers to any analytical technique based on the conjugation reaction of an antibody with an antigen. Examples of immunoassays known in the state of the art are, for example, but not limited to: immunoblot, enzyme-linked immunosorbent assay (ELISA), linear immunoassay (LIA), radioimmunoassay (RIA), immunofluorescence, x-map or protein chips.

In another preferred embodiment, the immunoassay is an enzyme-linked immunosorbent assay or ELISA. ELISA is based on the premise that an immunoreactive component (antigen or antibody) can be immobilized on a solid support, then putting that system in contact with a fluid phase containing the complementary reagent that can bind to a marker compound. There are different types of ELISA: direct ELISA, indirect ELISA or sandwich ELISA. In a preferred embodiment of this aspect of the invention, the ELISA is a sandwich ELISA.

As it is used herein, the term "marker compound" refers to a compound capable of giving rise to a chromogenic, fluorogenic, radioactive and/or chemiluminescent signal which allows detecting and quantifying the amount of antibodies against IFNAR2.3. The marker compound is selected from the list comprising radioisotopes, enzymes, fluorophores or any molecule susceptible of being conjugated with another molecule or detected and/or quantified directly. This marker compound can bind to the antibody directly or through another compound. Some examples of marker compounds that bind directly are, but not limited to, enzymes such as alkaline phosphatase or peroxidase, radioactive isotopes such as $^{32}P$ or $^{35}S$, fluorochromes such as fluorescein or metallic particles, for direct detection by means of colorimetry, autoradiography, fluorometry, or metallography, respectively.

Another aspect of the invention relates to a method for the diagnosis, prognosis and of classification of individuals, hereinafter third method of the invention, which comprises steps (a)-(c) according to the first method of the invention, and which further comprises assigning the individual of step (a) to the group of individuals with or without multiple sclerosis, depending on the cut-off point established for the sample index. Values with sample index above 2.14 (in the ROC curve) allows classifying the subjects as MS patients, whereas values less than 1.24 (in the ROC curve) are classified as healthy individuals.

In the onset of multiple sclerosis, there is a preclinical phase in which there are lesions, but no symptom manifestations. Suspected presence of the disease starts with the onset of the first clinically isolated syndrome (CIS).

Additionally, as demonstrated in Example 4 of the invention, sIFNAR2 can be used for the prediction or prognosis of the progression of CIS (clinically isolated syndrome) patients and for being able to determine in advance if the outbreak will be reverted or converted to multiple sclerosis.

Another aspect of the invention therefore relates to the use of siFNAR2 in the preparation of a marker for the prediction or prognosis of the progression of a CIS patient to multiple sclerosis.

As demonstrated in Example 4, sIFNAR has the capacity for making the prediction or prognosis that the patients have higher probability of converting to clinically defined MS (CDMS) after a clinical isolated syndrome (CIS). Another aspect of the invention therefore relates to a method, hereinafter fourth method of the invention, for the prediction or prognosis of the progression of a CIS patient to multiple sclerosis, which comprises steps (a)-(c) according to the first method of the invention, and which further comprises assigning the individual of step (a) to the group of individuals who will progress to MS, when they have greater and significant levels with respect to a reference sample. The reference sample is preferably obtained from patients who do not progress to MS.

Diagnostic Kit or Device and Uses Thereof

Another aspect of the present invention relates to a kit or device, hereinafter kit or device of the invention, comprising the elements necessary for quantifying the expression product of IFNAR2.3.

The kit or device of the present invention preferably comprises at least one anti-IFNAR2.3 antibody. In another preferred embodiment, the kit of the invention comprises secondary antibodies or positive and/or negative controls. In a much more preferred embodiment, the kit comprises the polypeptide of the invention produced by recombinant technology as positive control. The kit can furthermore include, without any limitation whatsoever, buffers, protein extraction solutions, agents for preventing contamination, protein degradation inhibitors, etc.

In addition, the kit can include all the supports and containers necessary for using and optimizing same. The kit preferably further comprises instructions for carrying out the methods of the invention.

In another preferred embodiment, the kit of the invention comprises:
  a) a solid support having a primary antibody bound thereto
  b) secondary antibody
  c) a solution of detection antibody labeled with an enzymatic marker;
  d) a reagent.

In an even more preferred embodiment, the primary antibody is an antibody comprising the amino acid sequence SEQ ID NO: 3

(MLLSQNAFIVRSLNLVLMVYISLVFGISYDSPDYTDESCTFKISLRNFR

SILSWELKNHSIVPTHYTLLYTIMSKPEDLKVVKNCANTTRSFCDLTDEW

RSTHEAYVTVLEGFSGNTTLFSCSHNFWLAIDMSFEPPEFEIVGFTNHIN

VMVKFPSIVEEELQFDLSLVIEEQSEGIVKKHKPEIKGNMSGNFTYIIDK

LIPNTNYCVSVYLEHSDEQAVIKSPLKCTLLPPGQESESAESAKIGGIIT

VFLIALVLTSTIVTLKWIGYICLRNSLPKVLRQGLTKGWNAVAIHRCSHN

ALQSETPELKQSSCLSFPSSWDYKRASLCPSD).

In another more preferred embodiment, the secondary antibody is an antibody comprising the amino acid sequence SEQ ID NO: 4

(MLLSQNAFIVRSLNLVLMVYISLVFGISYDSPDYTDESCTFKISLRNFR

SILSWELKNHSIVPTHYTLLYTIMSKPEDLKVVKNCANTTRSFCDLTDEW

RSTHEAYVTVLEGFSGNTTLFSCSHNFWLAIDMSFEPPEFEIVGFTNHIN

VMVKFPSIVEEELQFDLSLVIEEQSEGIVKKHKPEIKGNMSGNFTYIIDK

LIPNTNYCVSVYLEHSDEQAVIKSPLKCTLLPPGQESESAESAKIGGIIT

VFLIALVLTSTIVTLKWIGYICLRNSLPKVLRQGLTKGWNAVAIHRCSHN

ALQSETPELKQSSCLSFPSSWDYKRASLCPSD).

Another aspect relates to the use of the kit of the invention for the diagnosis, prognosis and classification of individuals having multiple sclerosis.

Another aspect of the invention relates to a computer-readable storage medium comprising programming instructions capable of making a computer carry out the steps of any of the methods of the invention (of the first or second method of the invention).

Another aspect of the invention relates to a transmissible signal comprising programming instructions capable of making a computer carry out the steps of any of the methods of the invention.

The first and/or the second method of the invention can include additional steps, such as for example, protein separation by means of one-dimensional electrophoresis and two-dimensional electrophoresis (2D-PAGE) or prior digestion of a protein mixture (from the sample) with trypsin for subsequently purifying and analyzing the peptides by means of mass spectrometry (MS), such as MALDI-TOF, or by means of multi-dimensional chromatography, by means of ICAT (Isotope-coded affinity tags), DIGE (Differential gel electrophoresis) or protein arrays.

The terms "polynucleotide" and "nucleic acid" are used interchangeably herein to refer to the polymeric forms of nucleotides of any length, both ribonucleotides (RNA) and deoxyribonucleotides (DNA).

The terms "amino acid sequence", "peptide", "oligopeptide", "polypeptide" and "protein" are used interchangeably herein to refer to a polymeric form of amino acids of any length, which can be chemically or biochemically modified coding or non-coding amino acids.

Throughout the description and the claims the word "comprises" and variants thereof do not intend to exclude other technical features, supplements, components or steps. For persons skilled in the art, other objects, advantages and features of the invention will be inferred in part from the description and in part from the practice of the invention. The following examples and drawings are provided by way of illustration and they are not meant to limit the present invention.

DESCRIPTION OF THE DRAWINGS

FIG. 13 shows several alignment sequences of the IFNAR2 extracellular domain with the isoform IFNAR2.3 and with the sequences recognizing the antibodies used in ELISA. The alignment was performed with the restriction-based multiple alignment tool (cobalt).

(B) Corresponding receiver operating characteristic curve for the diagnosis of MS based on serum sIFNAR2 levels (ROC).

Figure 16:
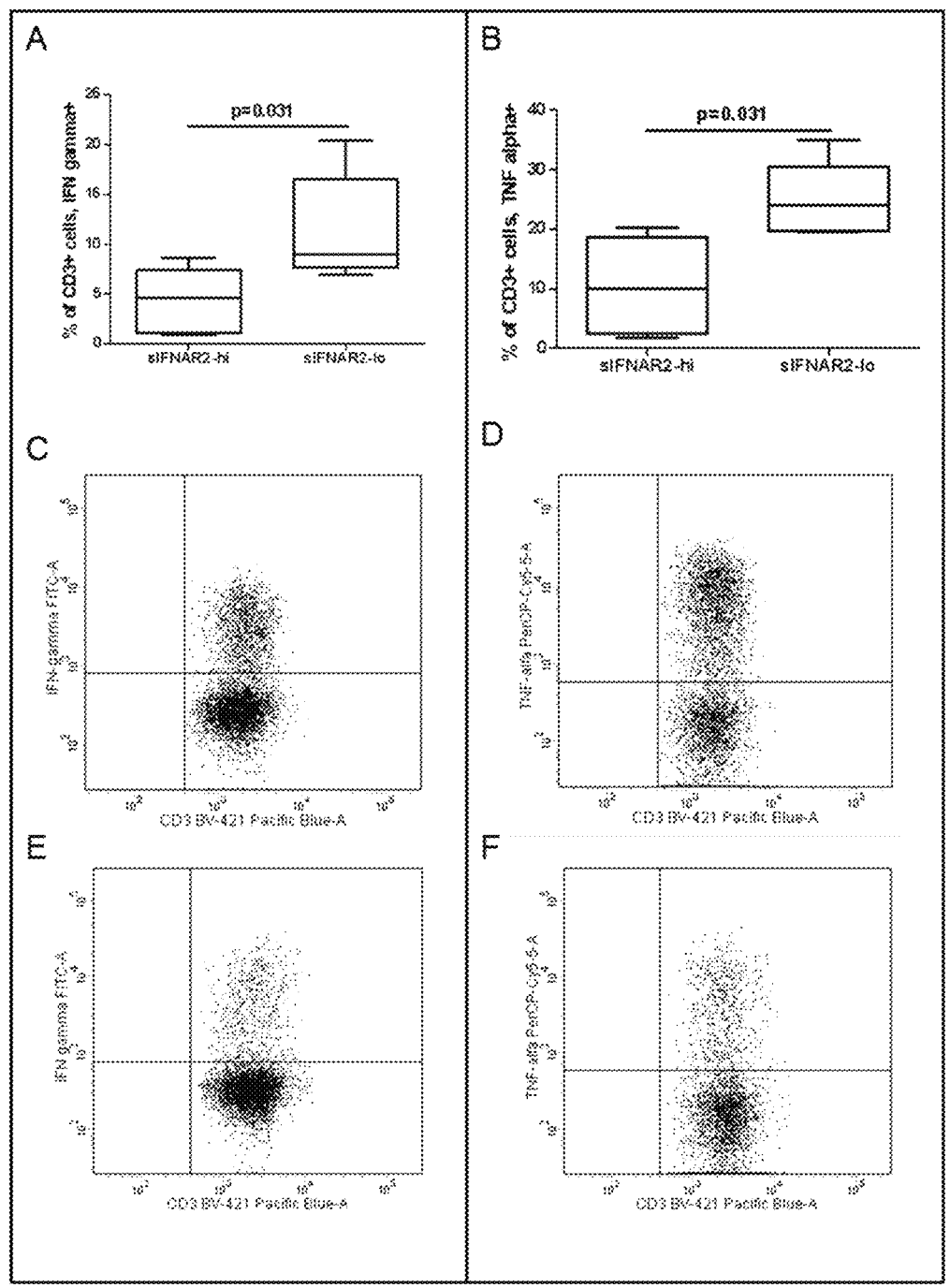

FIG. 16 shows the evaluation of IFN-gamma and TNF-alpha in patients with untreated MS The analysis of IFN-gamma (A) and TNF-alpha (B) expression in CD3+ cells of untreated MS patients with high and low sIFNAR2 level by flow cytometry.

The representative examples of IFN-gamma expression in a patient with low sIFNAR2 levels (C) and high sIFNAR2 levels (E). The representative examples of TNF-alpha expression in a patient with low sIFNAR2 levels (D) and high sIFNAR2 levels (F).

Figure 17:
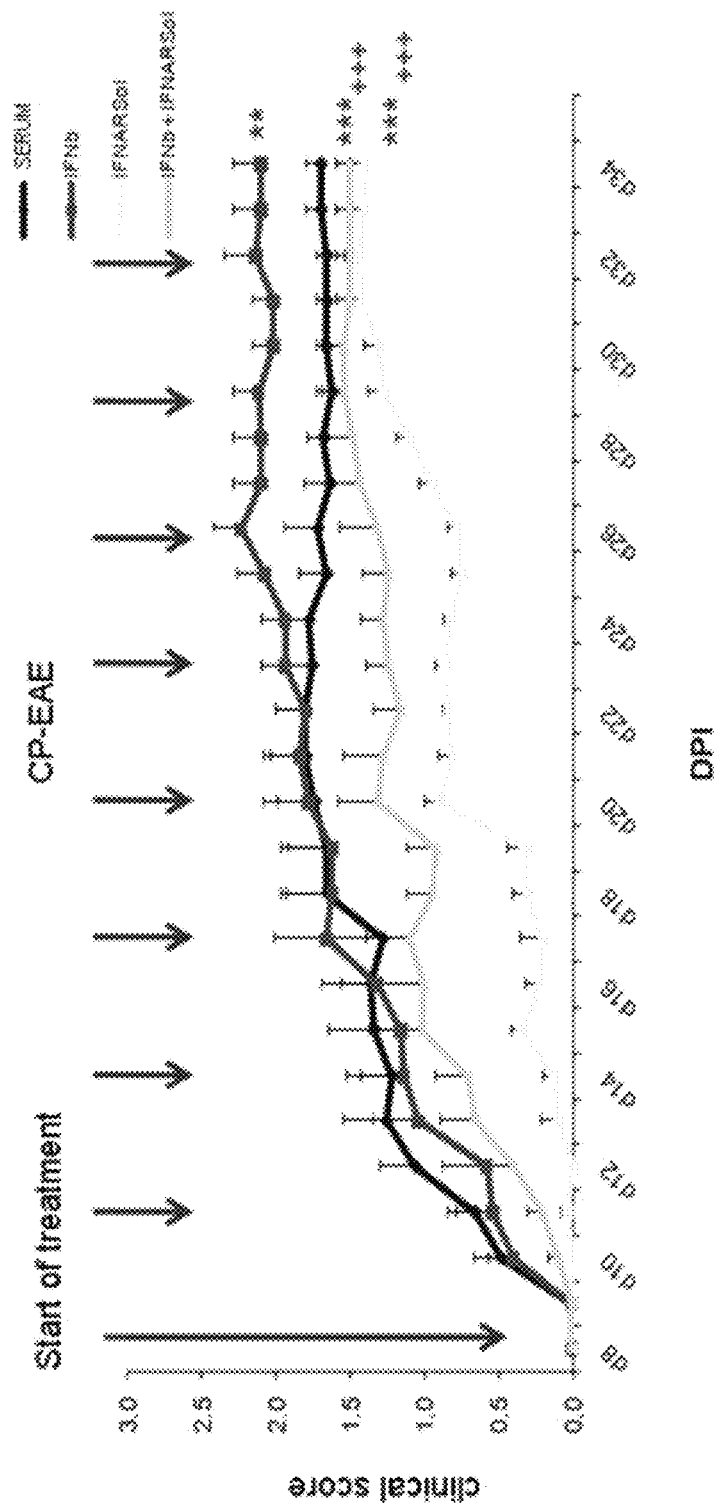

FIG. 17 shows a preventive treatment. One-way ANOVA+Newman-Keuls.

Figure 18:
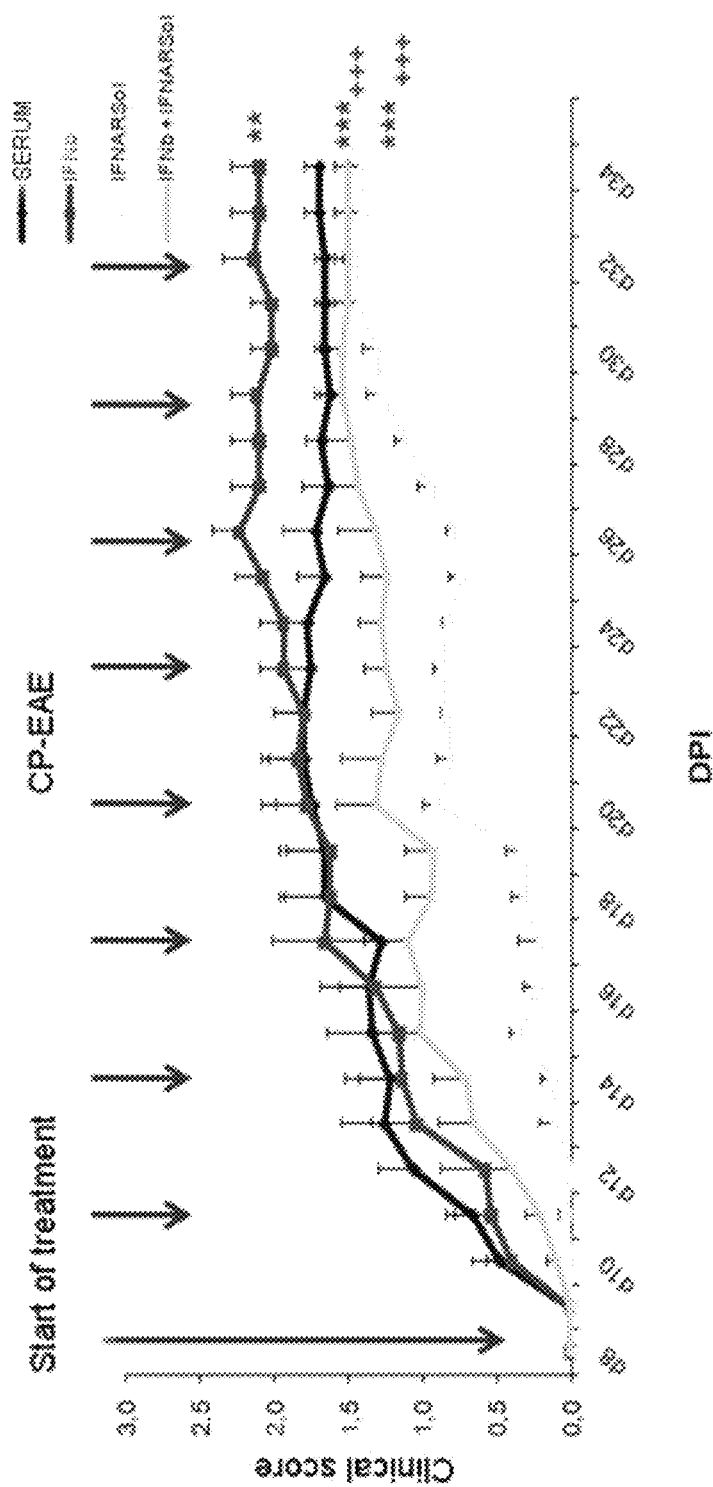

FIG. 18 show a preventive treatment. Paired T-Test.

Figure 19:
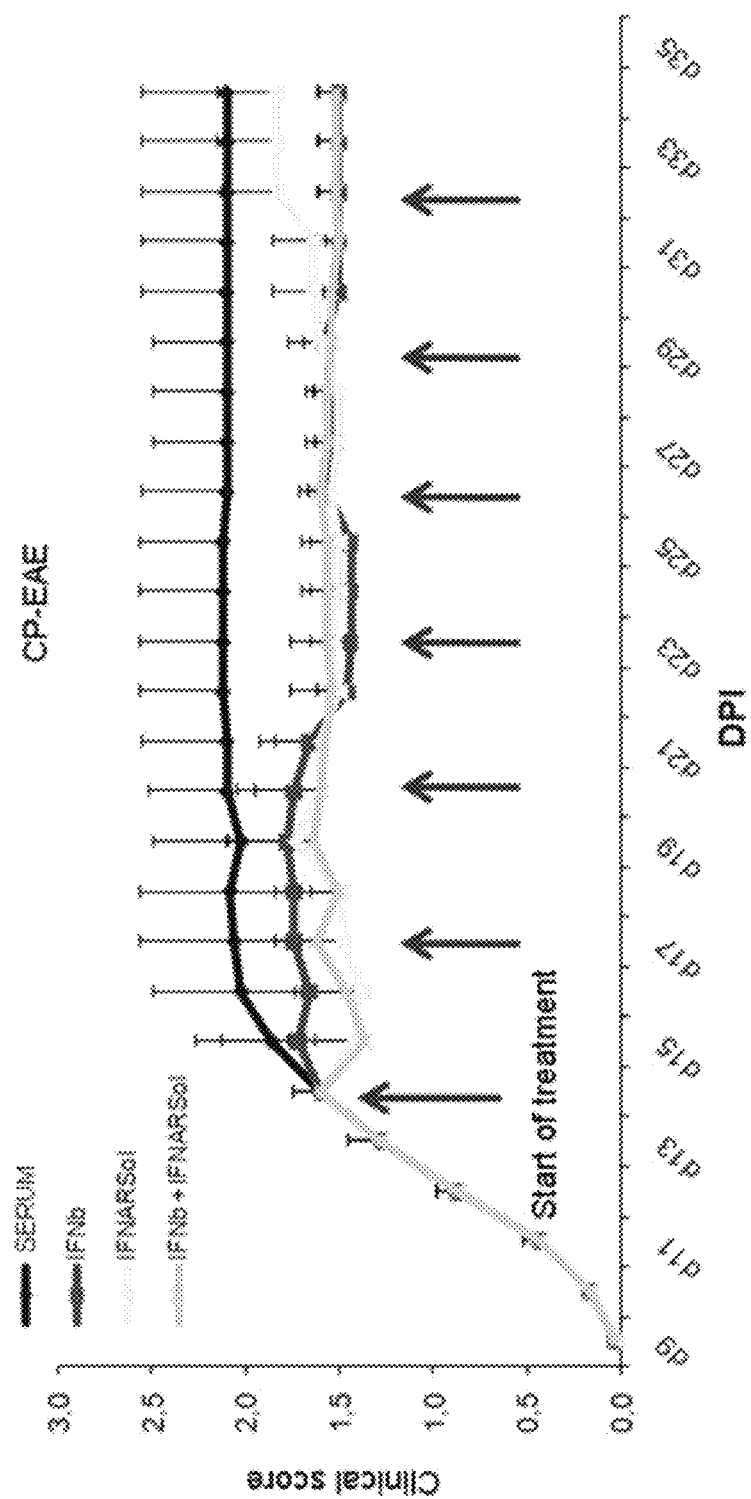

FIG. 19 shows a clinical treatment. One-way ANOVA+Newman-Keuls.

Figure 20:
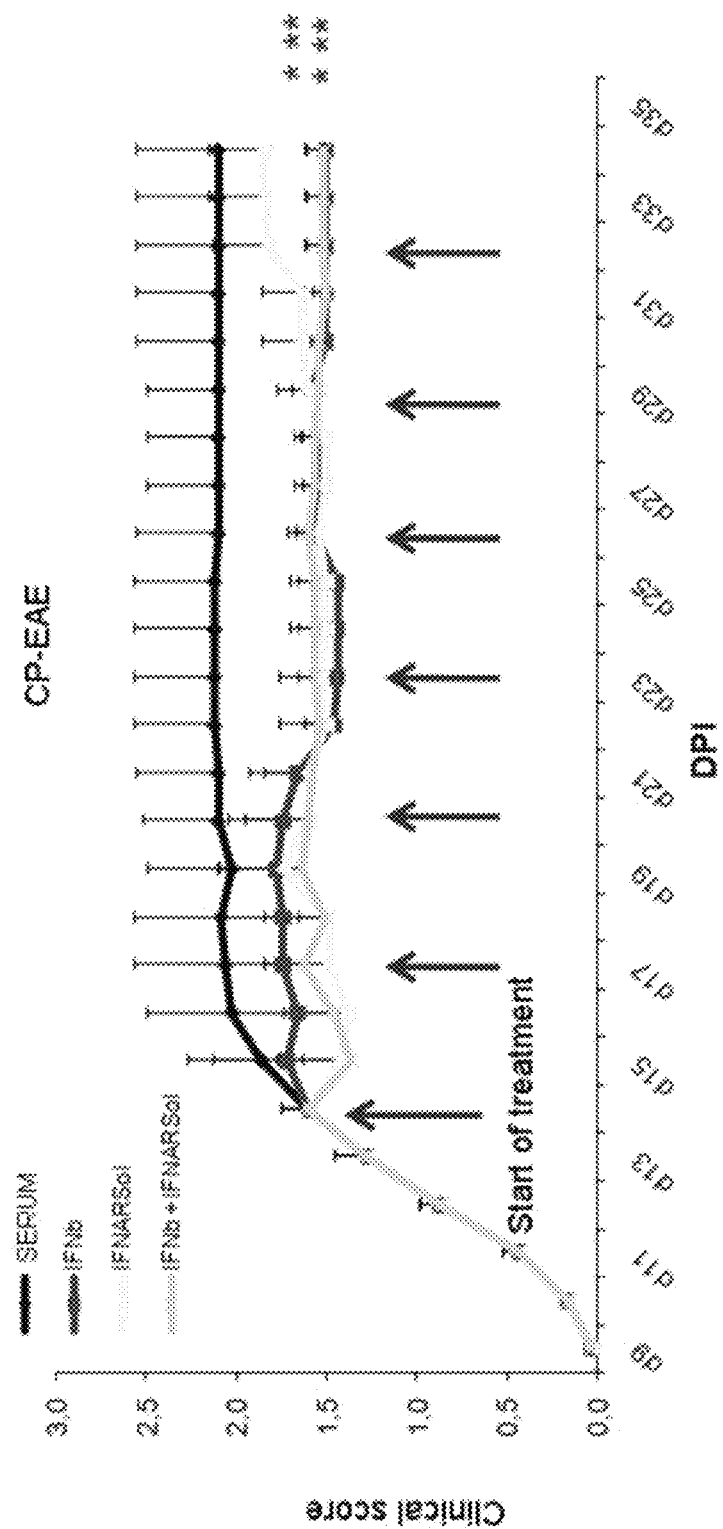

FIG. 20 shows a clinical treatment. Paired T-Test.

EXAMPLES

The invention will be illustrated below by means of assays performed by the inventors.

Materials and Methods
Recombinant Protein IFNAR2.3 Production
Cloning Vector Selection The chosen prokaryotic expression system is the prelinearized vector pEcoli-Cterm 6×HN Linear (Clontech). The resulting protein will be fused to a histidine-asparagine tag at the carboxyl-terminus that will be used for purification.

The images shown below provide the detail of the structure of the vector in which the insert with the nucleotide sequence of the protein of interest was integrated.

The pEcoli-Cterm 6×HN Linear expression system is based on the expression system of the strong T7 promoter controlled by the LacZ operon which is in turn inducible by IPTG (isopropyl-β-D-thiogalactopyranoside). The plasmid furthermore has an ampicillin resistance gene which allows selecting clones containing the plasmid.

The machinery of BL21(DE3) expression bacteria, using the T7 promoter, was used to produce the protein. The BL21(DE3) bacteria contain a chromosomal copy of the T7 RNA polymerase gene which is in turn under the control of the IPTG-inducible lacUV5 promoter.

DNA Insert Synthesis

The first point in designing the cloning strategy was insert synthesis. To that end, all the information about the sequence of IFNAR2.3, such as the peptide signal sequence, post-translational modifications, the biochemical characteristics of the protein, the domains thereof, etc., was collected. All this information was obtained from the UNIPROT database (www.uniprot.org/uniprot/P48551) which houses the amino acid sequences of the proteins and their biochemical characteristics.

IFNAR2.3 mRNA sequence was obtained from the NCBI NUCLEOTIDE database (www.ncbi.nlm.nih.gov/nuccore.)

Following the manufacturer's guidelines, the primers must meet the following requirements:

The 5' end:
containing 15 bases that are homologous to the 15 bases at the end of the DNA fragment of the vector in which it will be inserted.
The 3' end:
having 15 bases that are homologous to the ends of the gene that will be inserted.
a length between 18-25 bp and a GC content of 40-60%.
absence of start codon (ATG) and stop codon in the sequence to be amplified.
absence of signal sequence.

Taking these premises into account, the primers gave a 638-bp product after amplification. The sequences of the primers were:

Sense (sequence SEQ ID NO. 3):
5'TAAGGCCTCTGTCGACATTTCATATGATTCGCCTGATTACACGA

TG 3'

Antisense (sequence SEQ ID NO. 4):
5'CAGAATTCGCAAGCTTTGAAAATTCTGATTCCTGGCCAGGTGG

AA 3'

The insert is synthesized by means of conventional PCR from the primers designed in the preceding point using a high fidelity Taq and using a cDNA from a commercial human cDNA mixture as template. The optimum concentration conditions, temperature conditions and times for insert synthesis were the following:

TABLE 1 summary of the reagents of conventional PCR for insert synthesis

| Reagents | Volume/sample | Final concentration/sample |
|---|---|---|
| Rnase-free water | 40 μl | |
| Sense primer (20 μM) | 1 μl | 0.4 μM |
| Antisense primer (20 μM) | 1 μl | 0.4 μM |
| Dntp (10 μM) | 1 μl | 0.2 μM |
| Buffer 5X | 5 μl | 1X |
| Pfu High Fidelity | 1 μl | |
| cDNA | 1 μl | |

Temperature Conditions:

TABLE 2 summary of the temperature conditions for insert synthesis by means of Conventional PCR

| Stage | Temperature | Time | Cycles |
|---|---|---|---|
| Initial denaturation | 95° C. | 3 min | 1 |
| Denaturation | 95° C. | 20 sec | |
| Annealing | 60.4° C. | 20 sec | 40 cycles |
| Elongation | 72° C. | 30 sec | |
| Final elongation | 72° C. | 10 min | 1 |
| Final stage | 4° C. | Infinite | |

The end product obtained from the PCR was separated according to its size by means of horizontal electrophoresis technique in a 2% agarose gel dissolved in TAE buffer, together with Gold View Nucleic Acid Stain (Sbs Genetech) intercalating agent at a 1/20 dilution. The gel was subjected to a constant current of 80 V and was visualized in a UV-transilluminator which allowed locating the band of interest depending on the number of base pairs. The band located around 638 bp was cut out of the agarose gel with the help of a scalpel.

The amplified sequence of the insert contained in the agarose was purified with the commercial gel extraction kit (QIAquick Gel Extraction kit, QIAGEN) following manufacturer's indications. An eluate was obtained at the end of the process, said eluate was quantified with a spectrophotometer (Nanodrop, Thermo) before being stored at −20° C.

Ligation Process

Following the work diagram, the next point in the cloning process was the ligation process, i.e., "pasting" the nucleotide sequence of IFNAR2.3 to the plasmid, which will give rise to the recombinant protein.

To determine the concentrations and volumes of the insert and plasmid, the company Clontech offers through its web a computerized tool (bioinfo.clontech.com/infusion) for calculating the optimal amounts of the vector and insert for the ligation process from the known variables, vector and insert lengths.

To perform the ligation process, the insert mixture: plasmid was resuspended in the product In-Fusion Dry-Down pellet (Clontech). In-Fusion Dry-Down pellet is a lyophilisate containing the In-Fusion enzyme which favors the binding of the insert to the plasmid as a result of the homology in the nucleotide sequence present in both. The ligation reaction was carried out in a thermocycler at 37° C. for 15 minutes followed by 15 minutes at 50° C. and it was then transferred to ice. Finally, the ligation product was resuspended in 40 µl of TE buffer (Tris-HCl, EDTA) at pH 8.

Transformation into Replicative Bacteria

The competent bacteria used were MAX Efficiency DH5α™ Competent Cells (Invitrogen) which were transformed with the plasmid according to the following protocol:

As a positive control of the transformation technique, 5 µl of the pUC19 plasmid (positive control) were added into an aliquot of competent bacteria and this mixture was gently resuspended. At the same time, the bacteria were transformed with the ligation product. To that end, 2.5 µl were added to an aliquot of competent bacteria and mixed gently. Then both aliquots of bacteria (control and test) were incubated for 30 minutes in ice. After this time, the samples were subjected to heat shock at 42° C. for 45 seconds. The samples were quickly transferred to ice for 2 minutes and 900 µl of SOC medium (which favors the transformation process) were then added. For the plasmid to express ampicillin resistance, the samples were incubated at 37° C. under stirring of 225 rpm for 1 hour. Finally, the transformed bacteria were seeded at different volumes in LB-Agar plates supplemented with 100 µg/ml ampicillin and incubated overnight at 37° C.

Plasmid DNA Purification and Reading Frame Verification

After one night in the incubator, the bacteria had formed CFUs (colony forming units). To evaluate the characteristics of each CFU, the CFUs were isolated independently with the help of a seeding loop and seeded in tubes with 4 ml of LB broth supplemented with 100 µg/ml of ampicillin. These suspensions were incubated at 37° C. overnight under stirring of 220 rpm together with a negative control which was a tube of LB broth without bacteria. The plasmid contained in the bacteria was subsequently purified following the indications of the Promega kit (PureYield™ Plasmid Miniprep System) as explained below:

The bacterial culture was aliquoted in tubes of 1.5 ml and centrifuged at 16000 g for 30 seconds in a microcentrifuge. The supernatant was discarded from the obtained product and the precipitate was resuspended in 600 µl of water, to which 100 µl of cell lysis buffer was added and it was mixed by turning it upside down. 350 µl of neutralizing solution were added to this mixture and it was mixed again by turning it upside down. It was then centrifuged at 16000 g for 3 minutes. The supernatant obtained was transferred to one of the minicolumns provided in the kit which retains DNA. It was again centrifuged at 16000 g for 15 seconds. 200 µl of washing solution were then added to the minicolumn and it was centrifuged again for 15 seconds. 400 µl of washing solution were subsequently added to the minicolumn and it was centrifuged for 30 seconds. Finally, to elute the DNA which had been retained on the membrane, the minicolumn was transferred to a 1.5 ml clean microcentrifuge tube, 30 µl of sterile water were added to the center of the membrane and it was incubated for 1 minute at room temperature. Finally, to obtain the purified plasmid DNA, it was centrifuged at 16000 g for 15 seconds. The plasmid DNA was quantified by means of reading the absorbance in a spectrophotometer (Nanodrop, Thermo) and stored at −20° C. until the time of use.

At this point there were different isolated and frozen CFUs, but whether or not the plasmid had the insert, its complete sequence, the orientation in the open reading frame, etc., were unknown, therefore checking that the plasmid complies with all the desired requirements was required. To that end, two tests were performed:

Conventional PCR using the plasmid DNA as template DNA.

DNA sequencing: The positive plasmids in PCR were sequenced to obtain the nucleotide sequence which would allow evaluating the sequence of the insert and checking the orientation thereof.

Insert sequencing covered upstream sequences coinciding with the T7 promoter and downstream sequences coinciding with the T7 terminal sequence. The sequences obtained were aligned in the 5'-3' direction with the NBCI reference sequence having a GenBank number: CAA61940.1 by means of the Multalin bioinformatic software. The results obtained after the alignment confirming the sequence integrity and orientation in the correct reading frame is shown below:

Transformation into the BL21(DE3) Expression Bacteria

Once the clone containing the plasmid with the correct conditions was verified, the plasmid was transformed into the BL21(DE3) expression bacteria for the production of the recombinant protein IFNAR2.3, following the same protocol described previously for transformation into replicative bacteria and plasmid detection.

Induction of the Expression of the Recombinant Protein IFNAR2.3

Under normal conditions, the recombinant protein is not being expressed in the BL21(DE3) bacteria transformed with the plasmid because the expression thereof is repressed by the Lac repressor (LacI) which is bound to the Lac operon. To allow the expression thereof, IPTG which acts as an inducer sequestering the repressor and allowing the T7 RNA polymerase to bind to the T7 promoter and carry out the transcription process must be added. The protocol below was followed to induce the expression of the recombinant protein IFNAR2.3:

A day before inducing protein production, a preculture was prepared in the following manner:

The BL21(DE3) bacteria with the plasmid were cultured in 4 ml of LB broth supplemented with ampicillin at a final concentration of 100 µg/ml and incubated overnight at 37° C. under stirring of 220 rpm.

Induction of the expression of the protein was performed the next day. To that end, the culture from the day before was diluted 1/10 in a final volume of 50 ml of LB broth supplemented with ampicillin and incubated at 37° C. under stirring of 220 rpm until reaching an optical density (O.D.) of 0.80-1 nm. At this point, the IPTG inducer at a final concentration of 0.5 mM (previously established) was added and the culture was incubated for 4 hours at 37° C. under stirring of 220 rpm. The transcription process for the expression of the protein started from then on. The culture was collected 4 hours after induction (previously optimized) and centrifuged at 1600 g at 4° C. for 20 minutes. The supernatant was discarded and the pellet kept at −80° C. until later use.

Recombinant Protein Extraction

The expressed recombinant protein was found inside the bacterium. To access said protein and to be able to purify same, the bacterial wall must be broken by means of physical and chemical processes provided in detail below:

The bacterial precipitate stored at −80° C. was thawed at room temperature. 0.5 ml of bacterial lysis buffer were then added per milliliter of initial culture and it was resuspended with the help of a pipette. The resulting suspension was incubated for 1 hour at room temperature under rotation. After this time the sample was subjected to ultrasound in cycles of 5 30-second pulses in ice and with 40% intensity. It was then ultracentrifuged at 15000 g for 20 minutes at 4° C. and the membranes of the proteins released by the bacterium were thereby separated. After the ultracentrifugation, the supernatant was collected and passed through a 0.45-µm filter.

Recombinant Protein IFNAR2.3 Purification

The product obtained after the extraction contained the recombinant protein together with other bacterial proteins. The affinity chromatography technique was used to purify and isolate the recombinant protein IFNAR2.3, such that the recombinant protein IFNAR2.3 is retained through the histidine-asparagine tag it contains. The selected columns have a volume of 1 ml and are filled of Sepharose resin having nickel ions bound thereto. Nickel ions give the resin the capacity to retain histidine-rich proteins and therefore the recombinant protein IFNAR2.3 will be retained, among others. The protein is released from the resin by adding an imidazole-rich buffer which competes with the nickel binding site. The protocol followed is provided in detail below:

Before starting the purification process with affinity chromatography, the resin was washed and equilibrated with 10 ml of equilibration buffer. The protein extract containing the protein of interest was then contacted with the resin under rotation at 4° C. for 1 hour and the resin was subsequently packed in the column. To eliminate proteins that are not bound to the resin, the resin was washed with 10 ml of equilibration buffer. Finally, the proteins retained by the nickel were eluted with 5 ml of imidazole-rich elution buffer and collected in aliquots of 1 ml.

Recombinant Protein Detection: Electrophoresis and Western Blot

The first step for detecting the protein was to perform polyacrylamide gels electrophoresis and then transfer the proteins to a membrane. The protocol followed was:

The samples were resuspended in a 5× loading buffer and boiled at 100° C. for 3 minutes in a thermoblock. They were then loaded into a 12% polyacrylamide gel submerged in electrophoresis buffer and subjected to a constant current of 130 V. Once the electrophoresis ended, the gel obtained was submerged in transfer buffer for several minutes.

The transfer was performed in a semi-dry system in graphite sheets which had previously been wetted with water. The nitrocellulose membrane with a pore size of 0.45 µm was then activated by submerging it in water and subsequently equilibrated in transfer buffer. The sandwich was subsequently assembled; 9 transfer papers pre-wetted in transfer buffer were placed on the graphite sheet, then the membrane was placed on top and the gel which was going to be transferred was placed thereon. 9 transfer papers wetted in transfer buffer were placed again to finish off the sandwich. The transfer was performed for 45 minutes with an intensity of 0.8 mA/cm$^2$.

Once the transfer ended, the membrane was separated and blocked with blocking buffer for 2 hours at room temperature and under stirring. Blocking is a step that prevents the non-specific binding of antibodies to the free sites of the membrane, these sites being blocked with milk casein. After blocking, the membrane was contacted with 1/5000 human anti-IFNAR2 primary antibody produced in rabbit (Abnova), the dilution being established previously, in a blocking solution overnight at 4° C. under rotation. The membrane was removed from the solution with antibody the next day and washed with washing buffer. The membrane was incubated for 1.5 hours with rabbit anti-IgG antibody (Sigma-Aldrich) labeled with alkaline phosphatase at a dilution of 1/10000 in blocking solution. It was washed like in the preceding section. To see the result of the western blot, the membrane was developed by contacting it with a mixture formed by 200 µl of NBT/BCIP+10 ml of developing solution at room temperature until a colored product appeared. Finally, the reaction was stopped by discarding the developing solution and submerging it in a stopping solution that is rich in magnesium ions which block the colorimetric reaction by removing the NBT/BCIP.

Recombinant Protein Analysis

The recombinant protein sIFNAR2 was analyzed after being purified. To that end, protein band/bands were cleaved from an SDS/PAGE acrylamide gel and fragmented to perform the subsequent peptide fingerprinting analysis using MALDI-TOF/TOF mass spectrometry. The obtained results can be seen in FIGS. 10 and 11.

After purifying the protein, the assays for developing the ELISA technique were performed as provided in detail below.

ELISA Technique for Quantifying of Soluble IFNAR2.3 Fragment

The ELISA (enzyme linked immunosorbent assay) technique can be considered as one of the most powerful tools for detecting and quantifying specific proteins in a complex mixture thereof. It was originally described by Engvall and Perlmann in 1971 (Engvall & Perlmann *Immunochemistry.* 1971 September; 8(9):871-4) as a simpler and equally sensitive alternative to the methodology for detecting substances through RIA (radioimmuno assay).

A sandwich ELISA which requires two different antibodies that bind to the same antigen has been developed. The first antibody (bound to the plate) is referred to as primary antibody, whereas the second antibody detects the antigen immobilized by the first antibody and is referred to as secondary antibody). Given that this secondary antibody is not labeled, a third enzyme-conjugated antibody (species-specific) was used, the enzyme will then be contacted with its substrate to give rise to a colorimetric reaction.

The plate is sensitized with a specific antibody which will recognize and immobilize the antigen object of the study (IFNAR2.3). In this study, the concentration of primary antibody in combination with the concentration of secondary antibody has been optimized to increase the signal/background noise ratio. To that end, the plates were sensitized with three different concentrations of primary antibody (0.8, 1 and 1.2 µg/ml) in carbonate/bicarbonate buffer at pH 9.6 and incubated for 16 hours at 4° C. The primary antibody is subsequently removed and the plate is washed three times with TBS/Tween washing buffer (TBS, 1.5 mM $MgCl_2$, 0.05% Tween 20).

In all the experiments, non-specific binding was blocked by means of adding a blocking solution (TBS/Tween/1% BSA), incubating for 1 hour at 37° C., after which three washings with TBS-Tween are again performed.

To optimize the concentration of detection antibody, the plate was sensitized with the primary antibody as described above. The recombinant protein IFNAR2.3 produced in bacteria and purified by means of affinity chromatography was used as an antigen (and positive control of the technique). Different dilutions of the recombinant protein IFNAR2.3 (1/20, 1/50, 1/100 and 1/200) were used; furthermore a negative control was included in each plate consisting of blocking solution (TBS/Tween 20/1% BSA). The samples were incubated at 37° C. for 1 hour, after which the plate was washed three times with TBS/Tween buffer. After this step, the secondary antibody at different concentrations (400, 600 and 800 ng/ml in blocking solution) was added and it was incubated again for 1 hour at 37° C., the plate was then washed again 3 times with TBS/Tween buffer. It was subsequently incubated with an alkaline phosphatase-conjugated antibody following the supplier's specifications, the antibody specifically detecting the mouse IgG and it was again incubated for 1 hour at 37° C., the plate was washed after incubation with TBS/Tween. After this process ended, the alkaline phosphatase substrate solution was added to each well of the plate. After incubating the plate for 30 minutes at 37° C., the reaction was stopped with 3 M NaOH. As a result of the enzyme-substrate reaction, the wells in which identification of the antigen takes place appear bright yellow. The color intensity was quantified by reading the optical density of each well at 405 nm in a plate reader.

The result obtained in this type of experiments allowed fixing the optimum concentration of primary and secondary antibody to maintain the best signal/background noise ratio (drawings), selecting the sensitization of the plate with 0.8 μg/ml of primary antibody and 400 ng/ml of secondary antibody as the best condition.

Assay in Patients

Once the technique is optimized, the presence of IFNAR2.3 in serum in a first cohort of MS patients and healthy controls was determined.

|       |                     | Frequency | Percentage |
|-------|---------------------|-----------|------------|
| Valid | Untreated           | 81        | 60.4       |
|       | CONTROLS            | 53        | 39.6       |
|       | Total               | 134       | 100.0      |

A table (Table 3) is shown below as an example of the absorbances obtained:

|   | 1     | 2     | 3     | 4     | 5     | 6     | 7     | 8     | 9     | 10    | 11    | 12    |
|---|-------|-------|-------|-------|-------|-------|-------|-------|-------|-------|-------|-------|
| A | 0.999 | 0.876 | 0.813 | 0.812 | 0.709 | 0.722 | 0.928 | 0.939 | 0.862 | 0.835 | 0.743 | 0.778 |
| B | 0.747 | 0.665 | 0.672 | 0.733 | 0.787 | 0.768 | 0.8   | 0.776 | 0.686 | 0.702 | 0.995 | 1.056 |
| C | 0.882 | 0.85  | 0.841 | 0.829 | 0.729 | 0.735 | 1.032 | 0.845 | 0.706 | 0.759 | 1.045 | 1.012 |
| D | 0.711 | 0.721 | 0.701 | 0.7   | 0.915 | 0.906 | 0.6   | 0.618 | 0.726 | 0.966 | 0.96  | 0.983 |
| E | 0.89  | 0.832 | 0.925 | 0.877 | 0.897 | 0.866 | 0.709 | 0.676 | 0.843 | 0.949 | 0.917 | 0.892 |
| F | 0.872 | 0.814 | 0.839 | 0.825 | 1.106 | 1.118 | 0.639 | 0.661 | 0.767 | 0.776 | 0.764 | 0.75  |
| G | 0.941 | 0.954 | 0.839 | 0.86  | 0.933 | 0.94  | 0.758 | 0.743 | 0.984 | 1.014 | 0.842 | 0.827 |
| H | 0.967 | 0.972 | 0.874 | 0.89  | 0.808 | 0.817 | 0.88  | 0.919 | 4.000 | 3.909 | 0.208 | 0.205 |

The intra-assay variation of the technique has been calculated, determining the OD of the same sample in the same assay 12 times and a coefficient of variation of 12.2% has been obtained. To calculate the inter-assay variation, the OD of the same sample was determined in 7 different assays performed in different days, a coefficient of variation of 17.1% being obtained.

All the samples have been analyzed in duplicate. If the percentage of the coefficient of variation between the duplicates exceeds 25%, the determination for that sample is considered not valid.

Statistical Analysis of the Data

Figure 7:
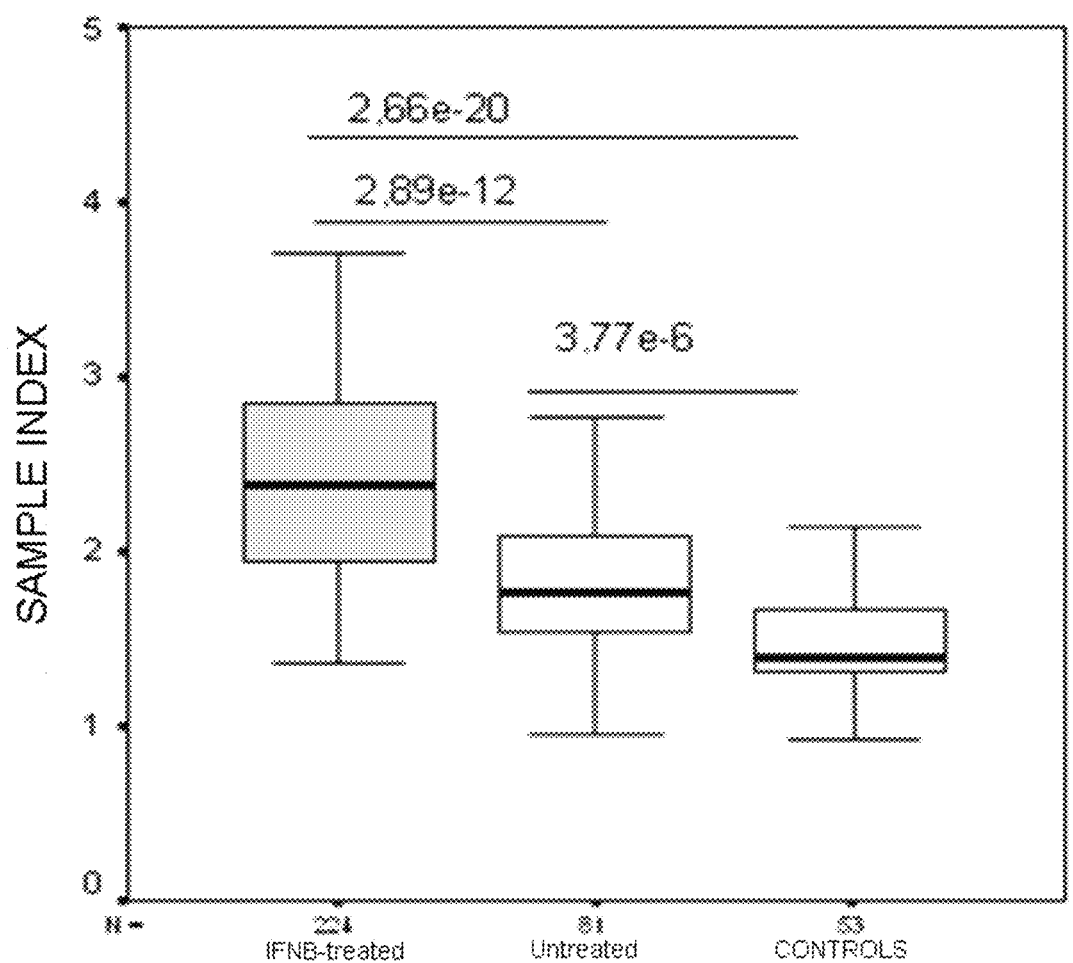
FIG. 7 shows an analysis of the values of IFNAR2.3 in serum in IFNβ-treated patients, untreated patients and controls.
Figure 8:
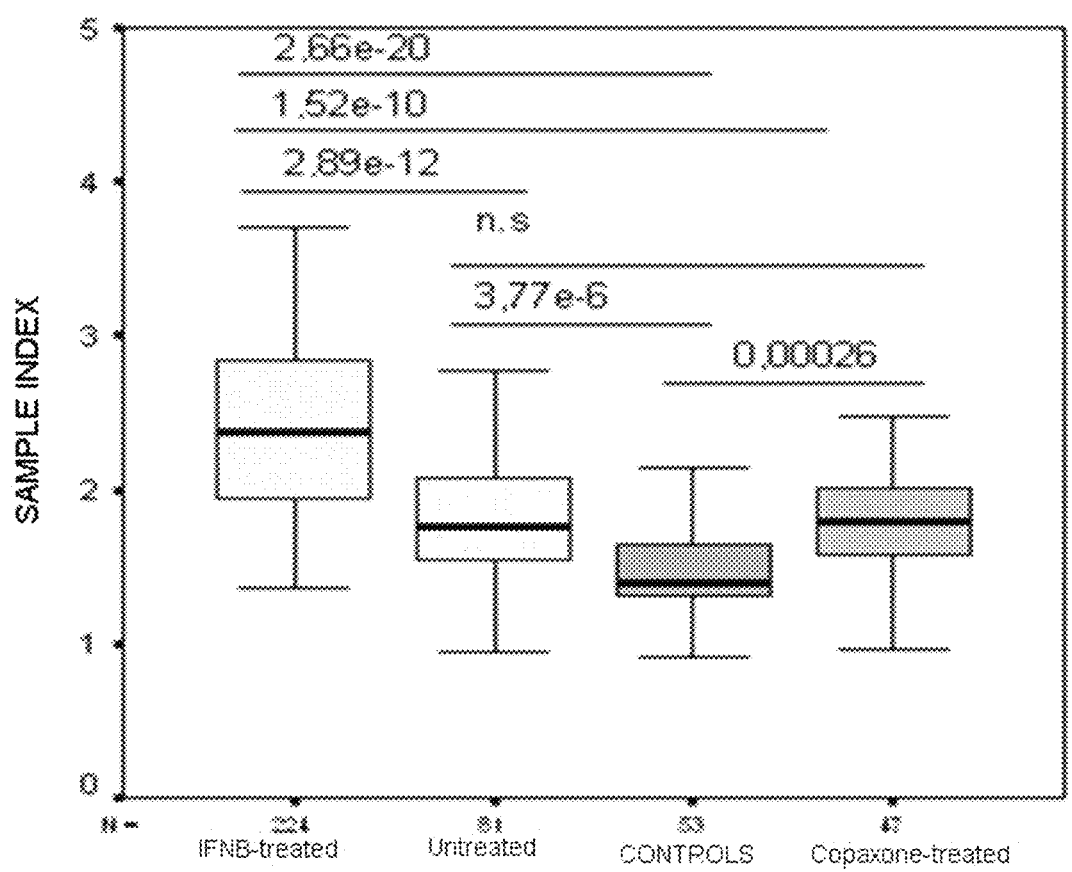
FIG. 8 shows an analysis of the values of IFNAR2.3 in serum in IFNβ-treated patients, untreated patients, controls and patients treated with Copaxone®.
Figure 9:
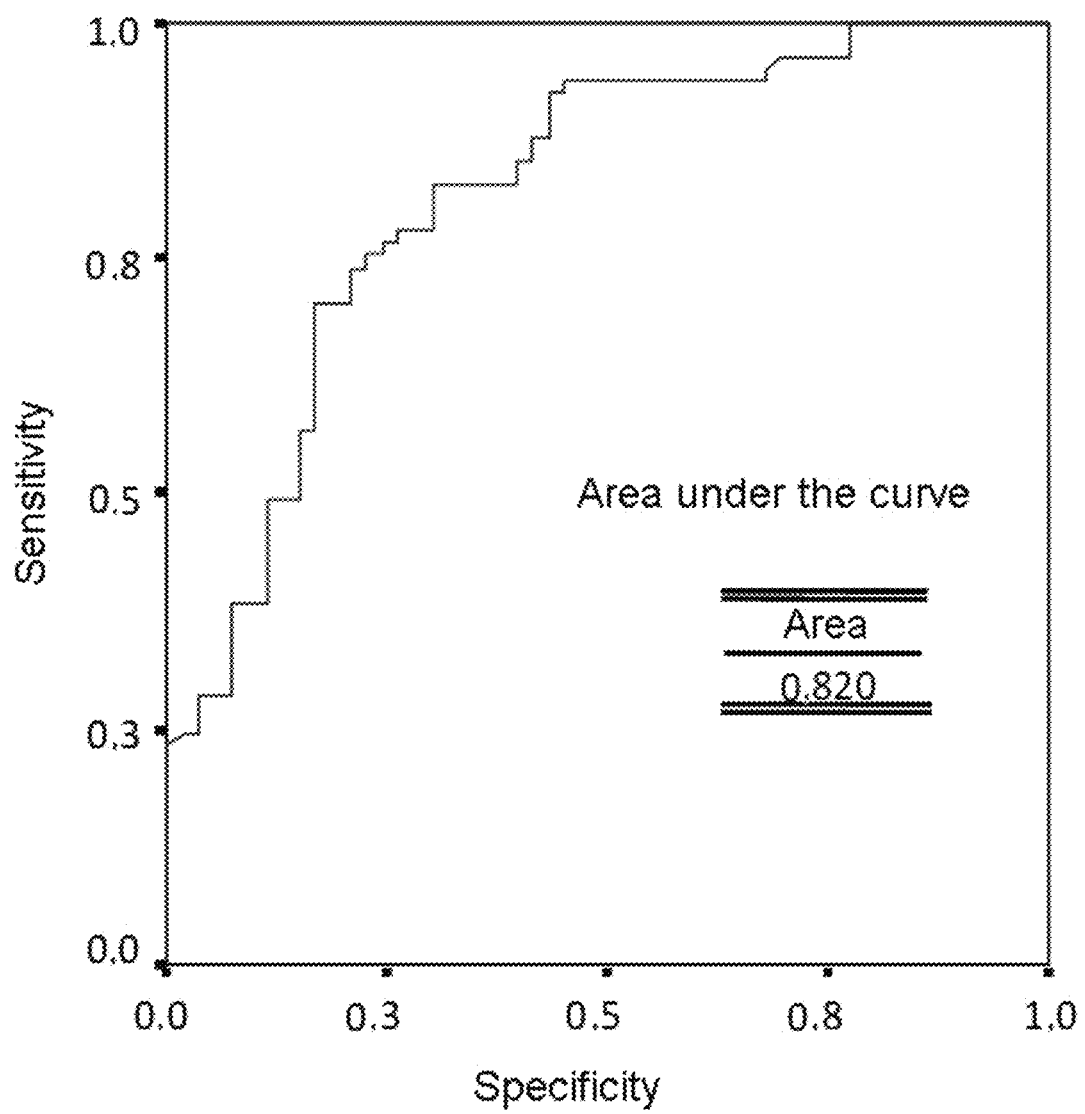
FIG. 9 shows a ROC curve for untreated patients and controls.

The data obtained in the different experiments were normalized for obtaining the "sample index" as described in the following section and non-parametric tests for independent samples were applied thereon. The expression of IFNAR2.3 in serum shows significant differences in patients treated with IFN, untreated MS patients and healthy controls, as seen in FIG. 7.

According to the data, treatment with IFNβ increases serum IFNAR2.3 levels with respect to untreated patients and healthy controls. The differences found between untreated patients and healthy controls, without the intervention of treatment with IFNβ, are probably due to the pathogenesis of the disease.

To check that the differences found are not due exclusively to treatment with IFNβ, patients treated with glatiramer acetate (Copaxone®) have been included. There were no significant differences between patients treated with Copaxone® and untreated patients (they have very similar medians) and the differences between patients treated with Copaxone® and healthy controls are maintained.

ELISA Sensitivity and Specificity Analysis

To normalize and homogenize the raw absorbance data obtained in the ELISA for determining IFNAR2.3 in serum, a cut-off point was established based on the negative control obtained in each plate, by means of the following calculations:

Cut off: 3(NEG OD+Neg Std Dev.); Cut off: 3(0.089+0.0136)=0.307

The absorbances of the sera were divided between the cut off. This new resulting value was referred to as the "SAMPLE INDEX" and it would be used to perform all the statistical analyses.

Sensitivity: Sensitivity is the probability of correctly classifying an individual who has been defined as positive with respect to the condition studied in the test. The probability that a sick subject obtaining a positive result in the test. Sensitivity is therefore the capacity of the test to detect the disease.

In this assay, the patient has been defined as positive.

Sensitivity=$TP/(TP+FN)*100$

Specificity: Specificity is the probability of correctly classifying an individual who has been defined as negative.

The probability of correctly classifying a healthy individual, i.e., the probability that a healthy subject obtaining a negative result. It is equal to subtracting the false positive fraction from 1.

In this case, the control has been defined as negative.

Specificity=$TN/(TN+FP)*100$

Different cut-off points have been arbitrarily established with the sample index. A new variable for each cut-off point has been created, classifying the samples as:

true positives (patients above the cut-off point)

false positives (control above the cut-off point), true negatives (control below the cut-off point)

false negatives (patients below the cut-off point).

Analysis of Treated Patients, Untreated Patients and Healthy Controls

MS patients (untreated patients, patients treated with IFN and patients treated with Copaxone®) and healthy controls (Figure IX) are included in this first analysis.

This analysis does not serve to discriminate between healthy controls and patients, because patients treated with IFN are included within the group of MS patients and it has been shown previously that treatment with IFN increases the IFNAR2.3 levels, so it is necessary to exclude IFNβ-treated patients from the analysis.

Analysis of Untreated Patients—Healthy Controls

Figure 10:
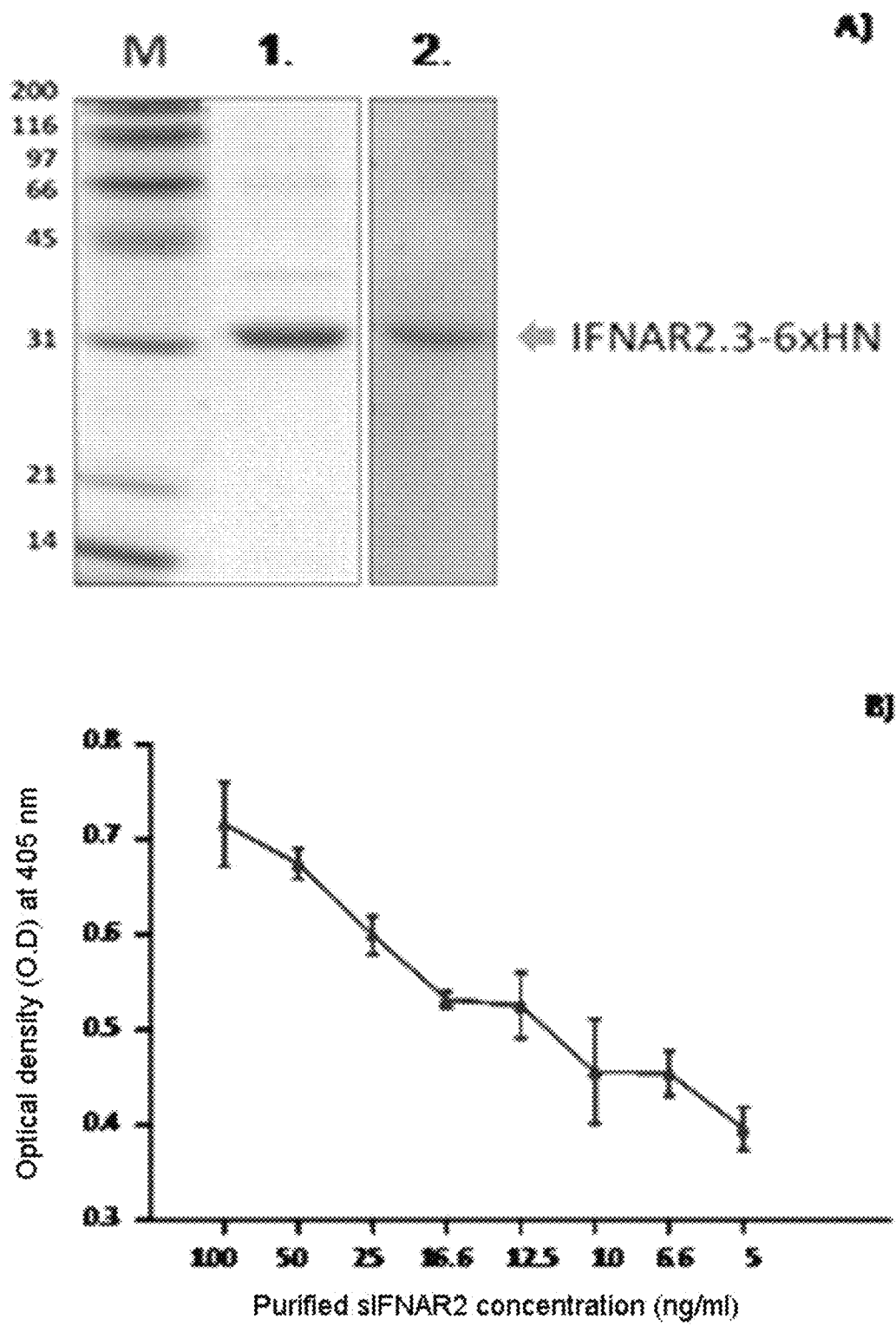
FIG. 10(A) shows the 12% SDS-PAGE and Western Blot of purified sIFNAR2 (30 kDa). M shows the molecular weight. SDS-PAGE of purified sIFNAR2 (column 1) and Western Blot of the same sequence (column 2). (B) Relationship between the concentration of purified sIFNAR2 and the optical density obtained by ELISA.

To establish if the test allows discriminating between MS patients and healthy controls, treated patients have been excluded from the analysis. (FIG. 10)

The sensitivities and specificities for different cut-off points are shown below according to the following formulas Sensitivity=$TP/(TP+FN)*100$ Specificity=$TN/(TN+FP)*100$

TABLE 4 positive = patient; negative = control; cut-off point 1.45

| | | Frequency | Percentage |
|---|---|---|---|
| Valid | true negative | 30 | 22.4 |
| | true positive | 74 | 55.2 |
| | false negative | 8 | 6.0 |
| | false positive | 22 | 16.4 |
| | Total | 134 | 100.0 |

Sensitivity = 90%
Specificity = 57%

TABLE 5 positive = patient; negative = control; cut-off point 1.50

| | | Frequency | Percentage |
|---|---|---|---|
| Valid | true negative | 36 | 26.9 |
| | true positive | 67 | 50.0 |
| | false negative | 14 | 10.4 |
| | false positive | 17 | 12.7 |
| | Total | 134 | 100.0 |

Sensitivity = 82.7%
Specificity = 67.9% positive = patient; negative = control; cut-off point 1.55

| | | Frequency | Percentage |
|---|---|---|---|
| Valid | true negative | 36 | 26.9 |
| | true positive | 65 | 48.5 |
| | false negative | 17 | 12.7 |
| | false positive | 16 | 11.9 |
| | Total | 134 | 100.0 |

Sensitivity = 79.2%
Specificity = 69.0% positive = patient; negative = control; cut-off point 1.70

| | | Frequency | Percentage |
|---|---|---|---|
| Valid | true negative | 39 | 29.1 |
| | true positive | 49 | 36.6 |
| | false negative | 33 | 24.6 |
| | false positive | 13 | 9.7 |
| | Total | 134 | 100.0 |

Sensitivity = 59.7%
Specificity = 75%

Summary of the Results

Taking into account the groups of untreated patients and healthy controls.

TABLE 6 frequency summary

| | | Frequency | Percentage |
|---|---|---|---|
| Valid | Untreated | 81 | 60.4 |
| | CONTROLS | 53 | 39.6 |
| | Total | 134 | 100.0 |

TABLE 7

SUMMARY Sensitivity and specificity of the variable, sample index (ELISA) with different established cut-off points (untreated patients and healthy controls)

| Cut-off point (Positive test) | Sensitivity (accuracy rate with patients) | Specificity (accuracy rate with controls) | |
|---|---|---|---|
| >1.24 | 100% | 25% | Patients are well classified |
| >1.45 | 90.0% | 57.0% | |
| >1.50 | 82.7% | 68.0% | |
| >1.55 | 79.2% | 69.0% | |
| >1.70 | 59.7% | 75.0% | |
| <2.14 | 24% | 100% | Controls are well classified |

TABLE 8

SUMMARY: Positive and negative predictive values of the variable, sample index (ELISA) with different established cut-off points
Positive predictive value: TP/TP + FP
Negative predictive value: TN/FN + TN

| Cut-off point (Positive test) | Positive predictive value* | Negative predictive value* | |
|---|---|---|---|
| <1.24 | | 100% | Detects all controls |
| <1.45 | 77.0% | 79.0% | |
| <1.50 | 79.7% | 72.0% | |
| <1.55 | 80.0% | 68.0% | |
| <1.70 | 79.0% | 54.0% | |
| >2.14 | 100% | | Detects all patients |

*Values subject to the prevalence obtained during consultation.

This is a case of a (univariate) indicator which, without other type of multivariate information, has good capacity for discriminating between MS patients and healthy controls.

The results obtained in the first cohort of patients which has been analyzed are reflected so far.

Example 2

Validation of sIFNAR2 as a Diagnostic Marker for MS

After the results obtained in the first cohort of patients, in which serum sIFNAR2 levels were evaluated in 305 multiple sclerosis (MS) patients (224 treated with IFNβ and 81 untreated) and 53 healthy controls, a second cohort was included to check if the data was replicated. This second cohort comprised 208 multiple sclerosis patients (136 treated and 72 untreated) and 64 healthy controls.

Recombinant sIFNAR2 was cloned and expressed in BL21(DE3) bacteria cells and purified with affinity columns. This protein was used for optimizing a non-commercial, semi-quantitative enzyme-linked immunosorbent assay for detecting sIFNAR2 and was included as a positive control in each series. The absorbance was normalized and the data was analyzed by means of the Mann-Whitney U test and ROC (receiver operating characteristics) curve.

Material and Methods
Subjects of the Study

The initial cohort included 305 patients recruited from Hospital Universitario Regional Carlos Haya (Malaga, Spain), with defined MS according to the criterion reviewed by McDonald (McDonald et al., 2001. *Ann Neurol* 50:121-7; Polman et al., 2005. *Ann Neurol* 58:840-6; Polman et al., 2011. *Ann Neurol* 69:292-302). 81 patients were previously treated and they had never received IFNβ, glatiramer acetate (GA) or mitoxantrone, or corticosteroids three months prior to blood sample withdrawal. In total, 224 patients had received treatment with IFNβ 1a or 1b for at least one year, and 47 patients had been treated with GA. 53 healthy individuals were selected as controls.

A second cohort of 136 treated MS patients, 72 untreated MS patients and 64 healthy controls was included to validate the preceding results.

The research protocol was approved by the Ethics Committee (CEI Malaga Nordeste) and all the participants gave their written informed consent.

Sample Collection

For untreated patients, 5 ml of peripheral blood were collected before starting treatment with IFNβ. For treated patients, samples were obtained after more than one year of treatment with IFNβ or GA. In all the cases, including the controls, serum was obtained by centrifugation at 1800×g for 5 minutes and stored at −20° C. until analysis thereof.

Cloning and Expression of Soluble Recombinant IFNAR2

The selected prokaryotic expression system was pEcoli-Cterm 6×HN Linear (Clontech®). The insert was synthesized by polymerase chain reaction using specific primers. The specific band was purified with the "QIAquick Gel Extraction" kit (QIAGEN®) and ligated with the "In-Fusion Dry-Down pellet" kit (Clontech®) following the manufacturer's instructions. Competent DH5a™ cells (Invitrogen®) were transformed, seeded in LB agar plates supplemented with ampicillin (100 mg/ml) and incubated overnight at 37° C. The colony forming units were isolated, seeded in lysogenic broth supplemented with ampicillin and incubated overnight under stirring. After purifying the plasmid (PureYield™ (Promega®)) and once the nucleotide sequence and the correct reading frame had been verified, BL21(DE3) bacteria (Invitrogen®) were transformed to produce the recombinant protein sIFNAR2. Once the culture reached an optical density (OD) of 0.8 ($\lambda$=600 nm), expression of the protein was induced by means of adding 0.5 mM of isopropyl β-D-1-thiogalactopyranoside with subsequent incubation for 4 hours at 37° C. under stirring. The bacteria were collected and resuspended in lysis buffer containing a protease inhibitor cocktail (Roche®), incubated for 30 minutes at room temperature under constant stirring and sonicated. The suspension was centrifuged at 20,000×g for 20 minutes at 4° C. and the supernatant was filtered.

The recombinant SIFNAR2 was purified in high capacity $Ni^{+2}$-iminodiacetic acid resin columns and detected by Western Blot using the anti-IFNAR2 human antibody MaxPab (Abnova®) (Table S1). The recombinant sIFNAR2 was also identified by MALDI ionization (matrix-assisted laser desorption ionization), coupled to a TOF (time-of-flight) analyzer (MALDI-TOF).

TABLE 10

Solutions used for cloning, expressing and purifying soluble recombinant IFNAR2 (sIFNAR2).

| SOLUTIONS | COMPOSITION |
|---|---|
| Lysis buffer | 50 mM Tris, 500 mM NaCl, 10% glycerol, 1% NP-40, pH 7 |
| Equilibration buffer | 50 mM sodium phosphate, 300 mM NaCl, 20 mM imidazole; pH 7.4 |
| Washing buffer | 50 mM sodium phosphate, 300 mM NaCl, 40 mM imidazole; pH 7.4 |
| Elution buffer | 50 mM sodium phosphate, 300 mM NaCl, 300 mM imidazole; pH 7.4 |

Determination of Soluble IFNAR2 in Serum by ELISA

Serum sIFNAR2 was detected by a non-commercial, semi-quantitative sandwich ELISA (Table S2). The plates were coated with anti-IFNAR2 human polyclonal antibody MaxPab produced in rabbit (Abnova®) at a final concentration of 800 ng/well and were incubated at 4° C. overnight. After washing the plate, 200 l of blocking buffer were added per well and it was incubated for 2 hours at room temperature. 50 l of the serum samples were then added in duplicate. After one hour, an anti-IFNAR2 human polyclonal secondary antibody MaxPab produced in mouse (Abnova®) (400 ng/well) was added and it was incubated for 1 hour. More details about the specificity of the antibodies used are included below and in FIG. 13.

Specificity of the antibodies used sIFNAR2 ELISA and information about IFNAR2 isoforms are found in: http://www.uniprot.org/uniprot/P48551

Anti IFNAR2 Human MaxPab H00003455-D01P (Abnova)

Rabbit polyclonal antibody raised against a full-length human IFNAR2 protein. IMMUNOGEN: IFNAR2 (AAH02793.1, 1 a.a. ~331 a.a) full-length human protein. SEQUENCE:

MLLSQNAFIVRSLNLVLMVYISLVFGISYDSPDYTDESCTFKISLRNFRS

ILSWELKNHSIVPTHYTLLYTIMSKPEDLKVVKNCANTTRSFCDLTDEWR

STHEAYVTVLEGFSGNTTLFSCSHNFWLAIDMSFEPPEFEIVGFTNHINV

MVKFPSIVEEELQFDLSLVIEEQSEGIVKKHKPEIKGNMSGNFTYIIDKL

IPNTNYCVSVYLEHSDEQAVIKSPLKCTLLPPGQESESAESAKIGGIITV

FLIALVLTSTIVTLKWIGYICLRNSLPKVLRQGLTKGWNAVAIHRCSHNA

LQSETPELKQSSCLSFPSSWDYKRASLCPSD

Anti IFNAR2 Human MaxPab H00003455-B01P (Abnova)

Mouse polyclonal antibody raised against a full-length human IFNAR2 protein. IMMUNOGEN: IFNAR2 (AAH02793.1, 1 a.a. ~331 a.a) full-length human protein. SEQUENCE:

MLLSQNAFIVRSLNLVLMVYISLVFGISYDSPDYTDESCTFKISLRNFRS

ILSWELKNHSIVPTHYTLLYTIMSKPEDLKVVKNCANTTRSFCDLTDEWR

STHEAYVTVLEGFSGNTTLFSCSHNFWLAIDMSFEPPEFEIVGFTNHINV

MVKFPSIVEEELQFDLSLVIEEQSEGIVKKHKPEIKGNMSGNFTYIIDKL

IPNTNYCVSVYLEHSDEQAVIKSPLKCTLLPPGQESESAESAKIGGIITV

FLIALVLTSTIVTLKWIGYICLRNSLPKVLRQGLTKGWNAVAIHRCSHNA

LQSETPELKQSSCLSFPSSWDYKRASLC

After washing the plate again, a rabbit anti-IgG antibody alkaline phosphatase produced in goat (Sigma-Aldrich®) diluted at 1/1000 was added and it was incubated for one hour. To develop the color reaction, a p-nitrophenyl phosphate (1 mg/ml) solution was added and it was incubated for 30 minutes. The OD was then measured at 405 nm. The value was made to be directly proportional to the amount of sIFNAR2 present in the serum.

TABLE 11

Solutions used in sIFNAR2 ELISA

| SOLUTIONS | COMPOSITION |
| --- | --- |
| Coating buffer | 0.015M carbonate-0.035M bicarbonate buffer pH 9.6 |
| Washing buffer | Tris buffered saline-0.5% Tween-20 1.5 mM Cl$_2$Mg pH 7 |
| Blocking buffer | 5 percent non fat dry milk in Tris buffered saline-0.5% Tween-20 pH 7 |

A non-diluted positive control with purified recombinant sIFNAR2 obtained as described above and a negative control containing only blocking buffer were included in each plate.

The cut-off point was established according to the following equation:

$$3(\text{mean O.D.}_{negative} + \text{mean standard deviation (SD)}).$$

The absorbance of the serum samples were normalized as follows:

O.D.$_{sample}$/3 (mean O.D.$_{negative}$+SD) and the result was designed as the sIFNAR2 index.

Statistical Analysis

The data are presented as median and interquartile range. Since a non-normal distribution was established in the Kolmogorov-Smirnov test, non-parametric methods were used for statistical comparisons.

The statistical differences between the independent groups were calculated using the Kruskal Wallis test (more than two independent variables) with the Mann-Whitney U test (two independent variables). Statistical significance was established at $p \leq 0.05$.

ROC (Receiver Operating Characteristic) curve analysis was used for evaluating the diagnostic capacity of sIFNAR2 for identifying MS patients. The sensitivity, specificity and cut-off values were calculated using the area under the curve (AUC) according to standard formulas.

Results

Patient Characteristics

The demographic and clinical characteristics are summarized in Table 12.

| | Cohort original untreated | Cohort of validation untreated | p-value |
| --- | --- | --- | --- |
| n | 81 | 72 | |
| Female/male | 53/28 | 42/30 | 0.41 |
| Mean age at the onset of symptoms (years) | 26 (5.91) | 29 (10.75) | 0.89 |
| Duration of the disease (years) | 10.13 (6.61) | 9.67 (8.65) | 0.32 |
| Clinical form RR/SP | 47/34 | 62/10 | 0.914 |
| EDSS score at the onset[a] | 2 (2.0) | 1.75 (1.69) | 0.123 |

Figure 11:
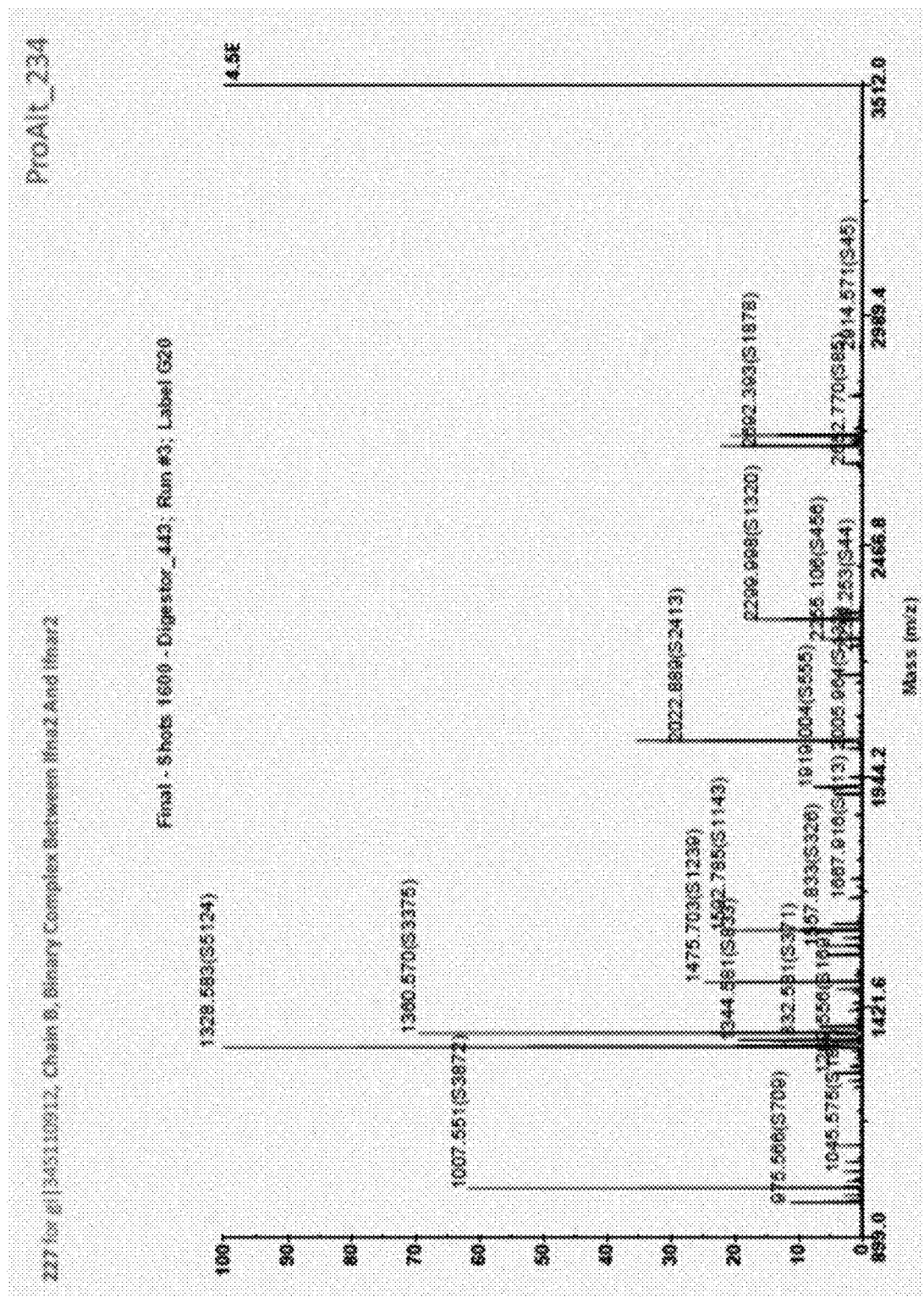
FIG. 11 shows the result of the peptide fingerprinting analysis using MALDI-TOF/TOF mass spectrometry.

[a]The data is expressed as mean (standard deviation), p-values were obtained through the following comparisons between means of chi-square test (sex and clinical presentation) and RR: Relapsing-Remitting; SP: Secondary Progressive; EDSS: Expanded Disability Status Scale Sandwich ELISA for the Detection of sIFNAR2 in Serum The antibody concentrations used in ELISA were optimized for obtaining the best signal/noise ratio. The specificity of ELISA was confirmed by means of obtaining positive results in wells containing recombinant sIFNAR2 and negative results from samples without recombinant sIFNAR2. The absorbance decreased linearly with higher sIFNAR2 dilutions (FIG. 11).

The intra- and inter-assay variability was evaluated, obtaining a coefficient of variation of 5.3% and 14.8%, respectively.

Evaluation of Serum sIFNAR2 Levels in MS Patients and Healthy Controls.

Figure 1:
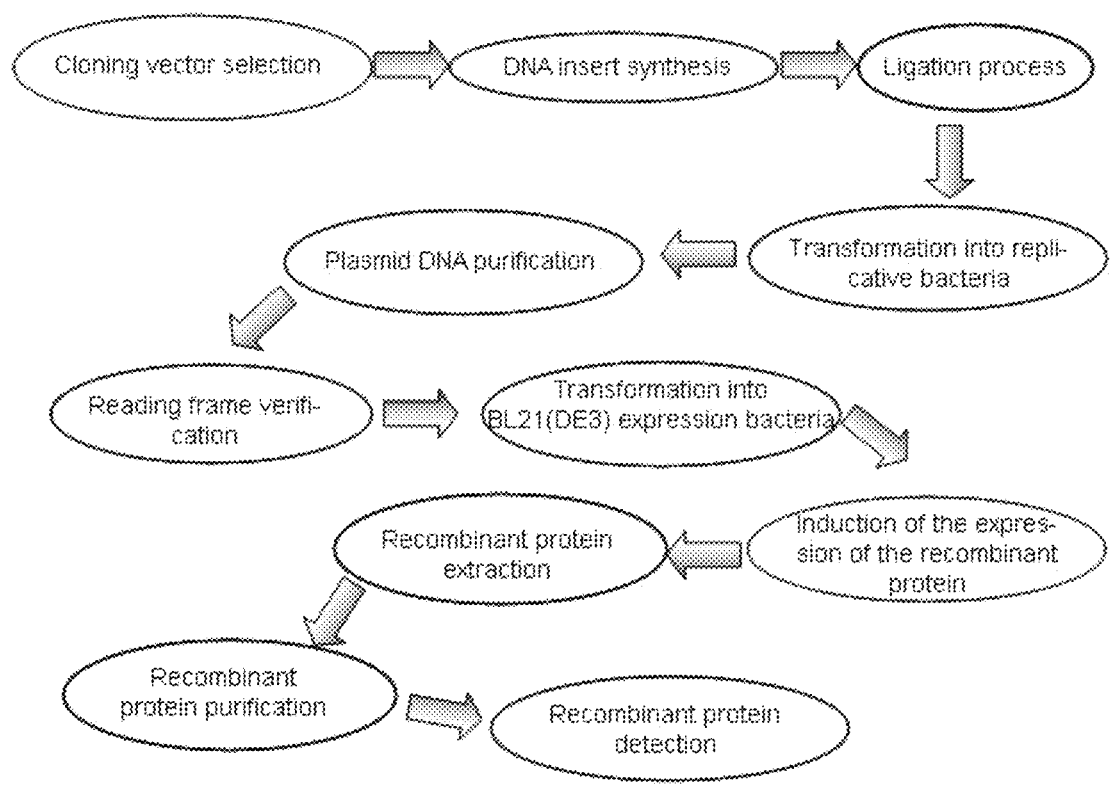
FIG. 1 shows the work diagram for cloning, producing and purifying the recombinant protein.
Figure 2:
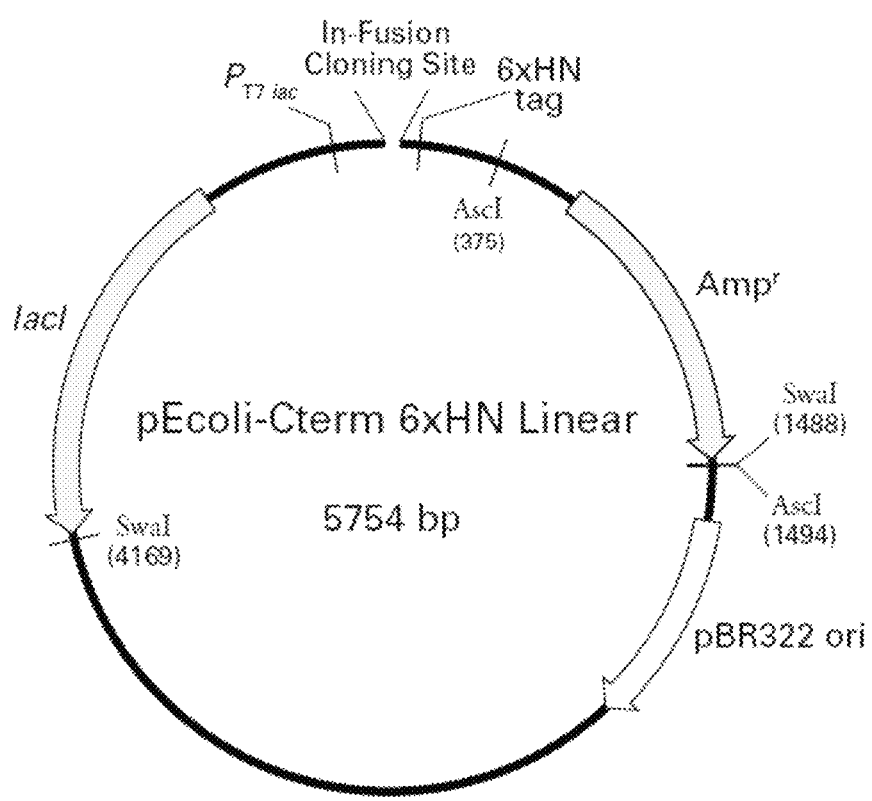
FIG. 2 shows the structure of the pEcoli-Cterm 6×HN Linear vector.
Figure 3:
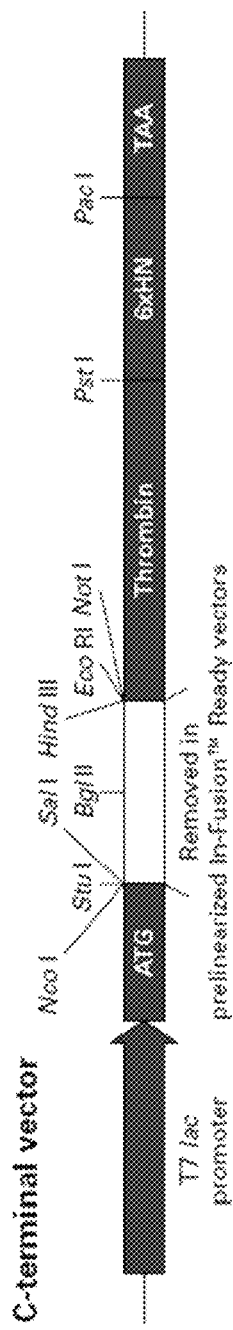
FIG. 3 shows the structure of the structures flanking the insert.
Figure 4:
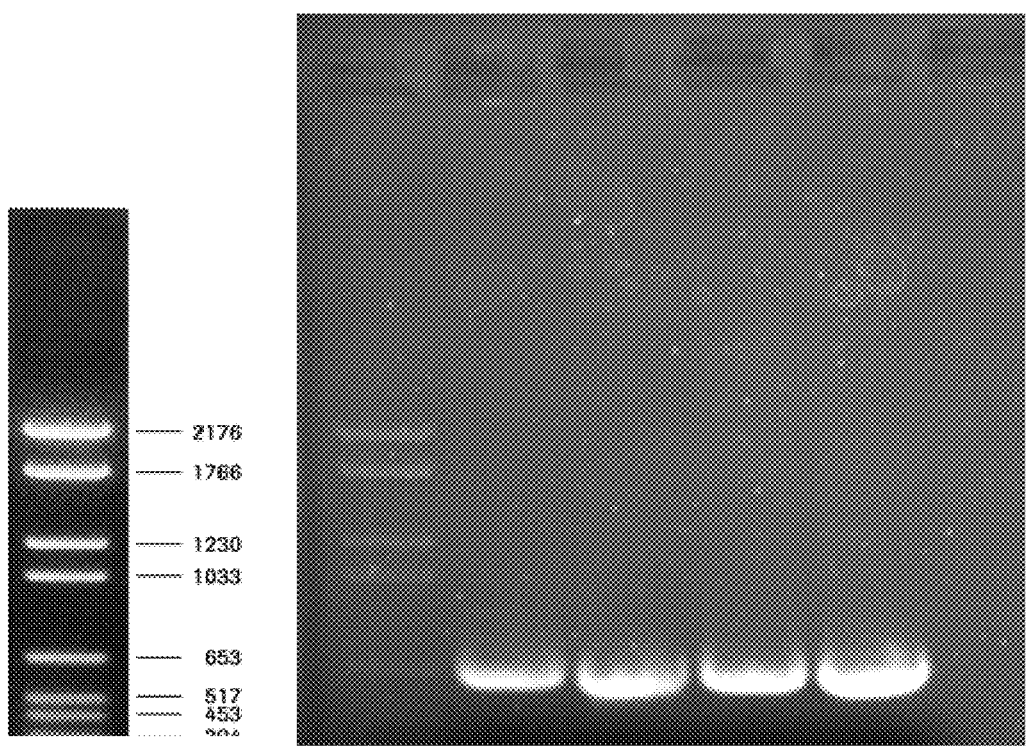
FIG. 4 shows an agarose gel electrophoresis of the amplified component obtained by PCR.
Figure 5:
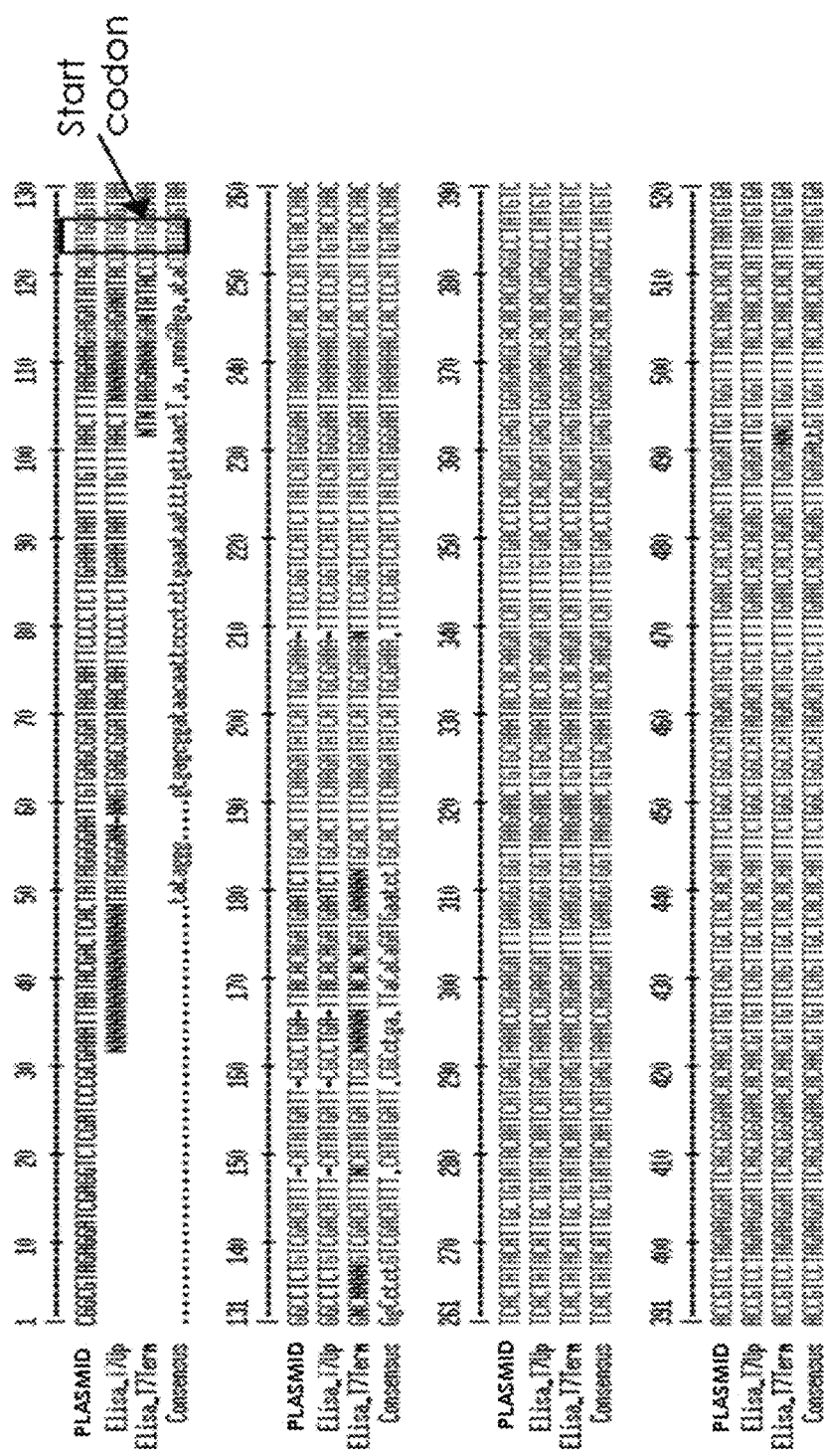
FIG. 5 shows alignments of the nucleotide sequences in the 5'-3' direction. The first line shows the nucleotide sequence of IFNAR2.3, the second and third lines show the nucleotide sequences with the flanking primers of the T7UP and T7terminal inserts, obtained after the plasmid sequencing process.
Figure 5:
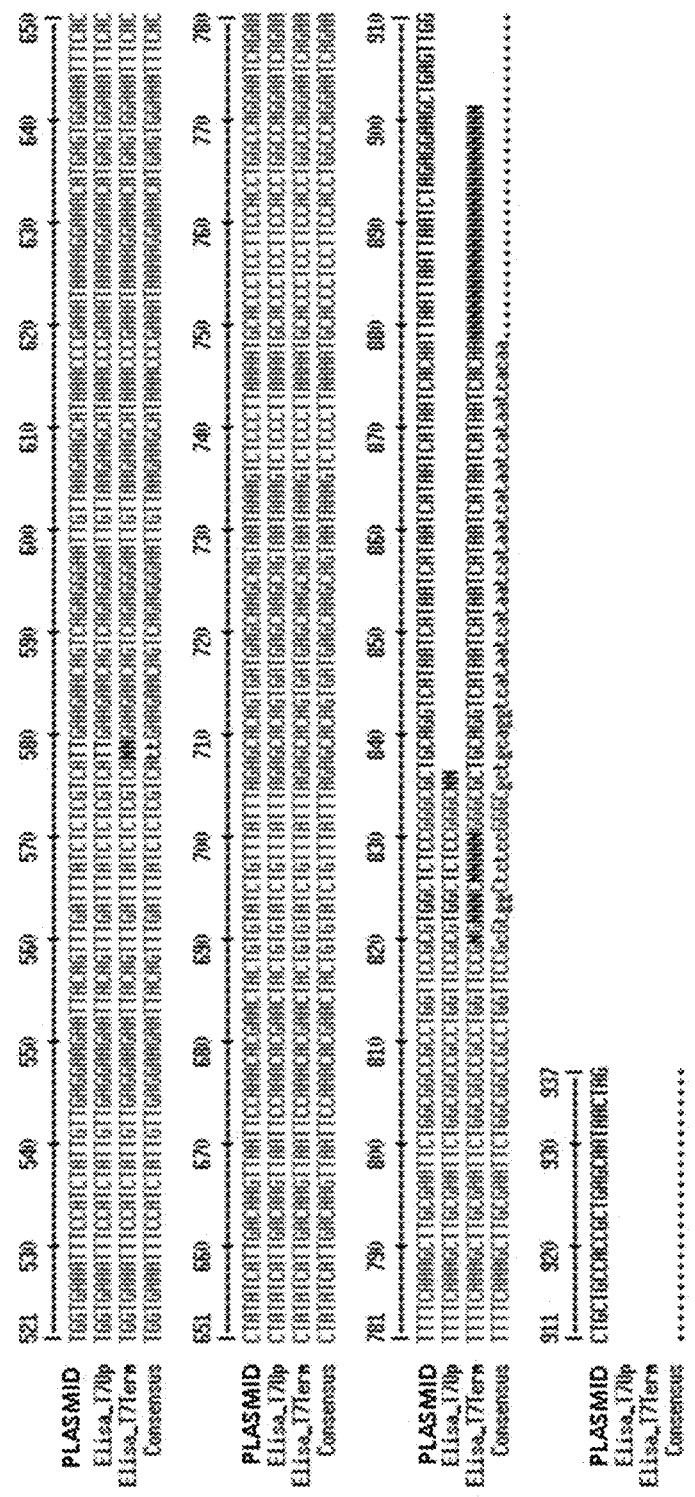
Figure 6A:
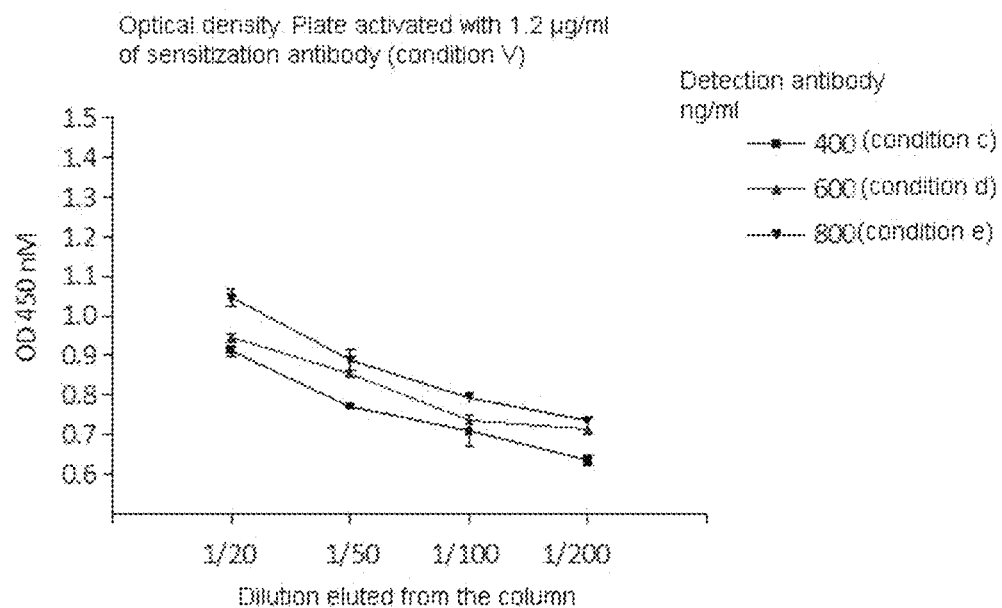
FIG. 6 shows graphs of the development of the antibody concentrations for ELISA for determining IFNAR2.3 in serum. (A). Absorbances obtained with 1.2 µg/ml of primary antibody vs. different concentrations of secondary antibody (B). Absorbances obtained with 1 µg/ml of primary antibody vs. different secondary antibody concentrations. (C). Absorbances obtained with 0.8 µg/ml of primary antibody vs. different secondary antibody concentrations (D). Graph showing the linear relationship between absorbance and protein IFNAR2.3 concentration.
Figure 6B:
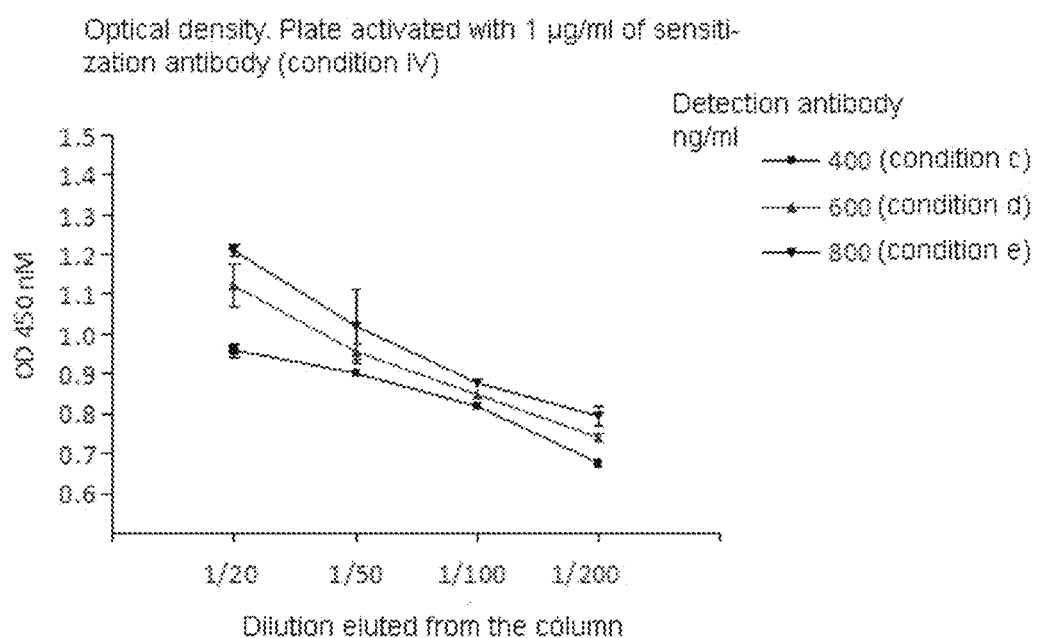
Figure 6C:
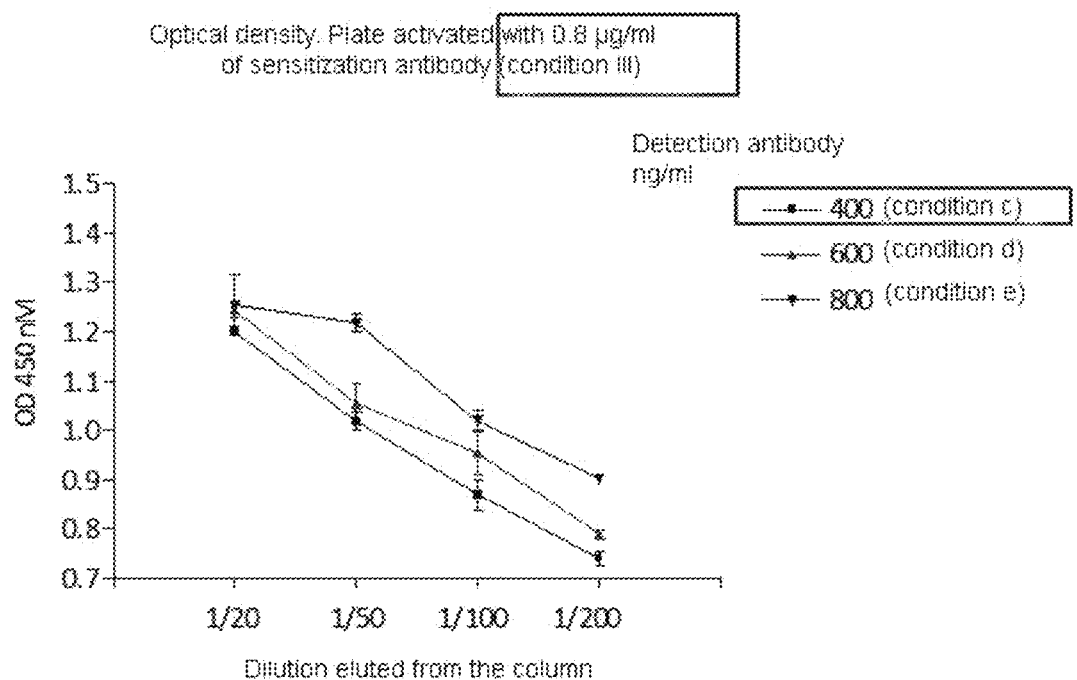
Figure 6D:
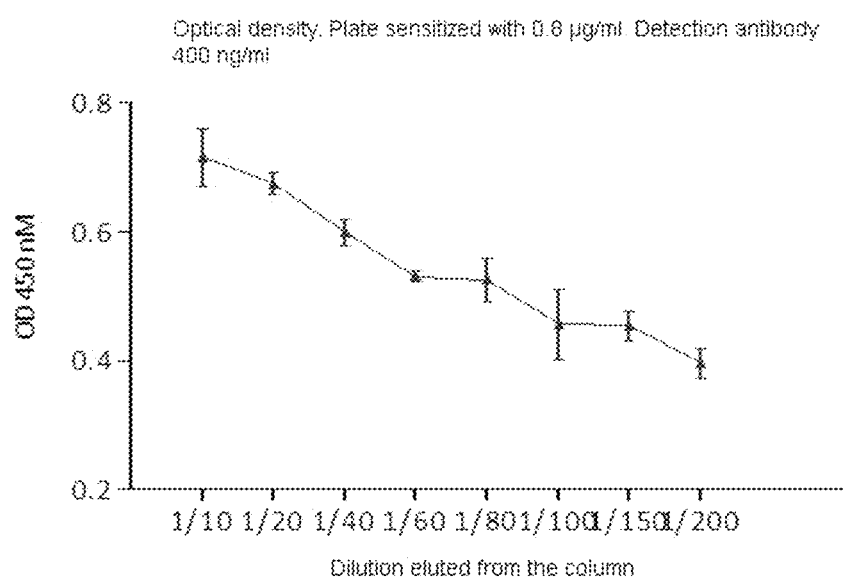

The comparison of MS patients and healthy controls in the first cohort showed a significant increase in serum sIFNAR2 levels in patients compared with healthy controls (P<0.001) (FIG. 2). The sIFNAR2 values obtained for the different groups under study are summarized in Table 13.

TABLE 13

The median and the interquartile range of sIFNAR2 determined by ELISA.
IFNβ: interferon beta; GA: Glatiramer acetate

|  | Original cut-off | Validation cut-off | Pooled analysis |
|---|---|---|---|
| Treatment for MS | 2.15 (1.79-2.72) | 1.54 (1.09-2.23) | 1.97 (1.52-2.61) |
| IFNβ-treated | 2.37 (1.93-2.84) | 1.48 (1.12-2.07) | 2.07 (1.54-2.71) |
| Untreated | 1.80 (1.58-2.08) | 1.69 (0.94-2.53) | 1.76 (1.47-2.23) |
| GA-treated | 1.79 (1.50-2.00) | | |
| Healthy controls | 1.37 (1.22-1.56) | 1.12 (0.88-1.52) | 1.31 (0.98-1.53) |

Figure 15:
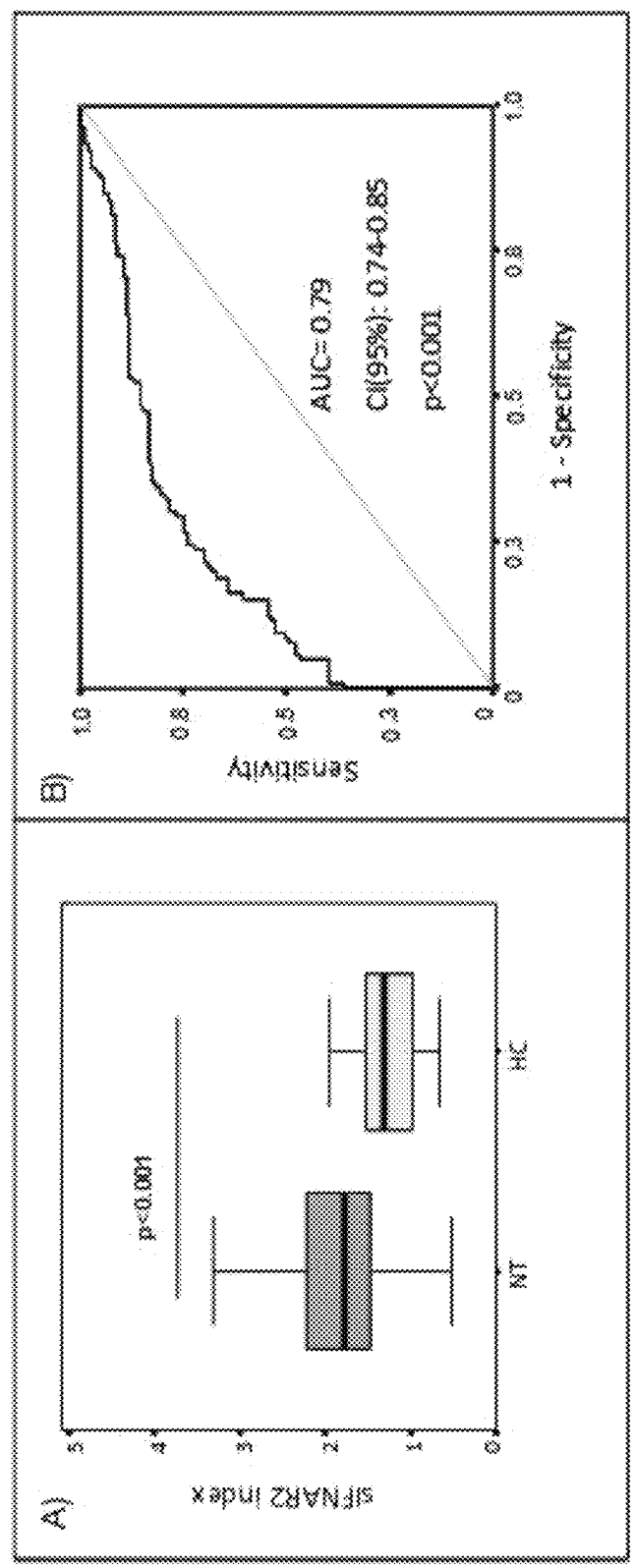
FIG. 15 shows the evaluation of sIFNAR2 as a diagnostic marker (A) the semi-quantitative values of sIFNAR2 in the serum of untreated MS patients (NT) and healthy controls (HC) of pooled cohorts.

MS patients were divided into two groups, IFNβ-treated and IFNβ-untreated, to evaluate the effect of treatment with IFN on serum sIFNAR2 levels. IFNβ-treated patients show a significant increase in serum sIFNAR2 levels compared with untreated patients (P<0.001) and with healthy controls (P<0.001). To confirm that the increase in sIFNAR2 observed in treated patients was due to the action of IFNβ, a group of GA-treated patients was included. These patients show significantly lower serum sIFNAR2 levels compared with IFNβ-treated patients (P<0.001) and higher serum levels compared with healthy controls (P<0.001). However, no differences were observed between untreated patients and GA-treated patients (FIG. 15A).

Curiously, the untreated patients had significantly higher sIFNAR2 values than healthy controls (P<0.001). This suggests that this soluble receptor could be a potential diagnostic biomarker for MS. To corroborate these results, sIFNAR2 in serum was determined in a second independent cohort. The differences in serum sIFNAR2 levels between untreated patients and healthy controls are reproduced in this second study (P<0.001) (FIG. 15B). However, the differences between treated and untreated patients which are observed in the first cohort did not reach a significant value in the second cohort studied, probably due to data dispersion in this substudy.

In the pooled analysis of both cohorts, treated patients had increased sIFNAR2 levels compared with untreated patients (P<0.001) and healthy controls (P<0.001). As was expected, the pooled results showed higher sIFNAR2 levels in untreated patients compared with healthy controls (P<0.001) (FIG. 15A).

Evaluation of Soluble IFNAR2 as a Diagnostic Biomarker for MS

The differences observed between untreated patients and healthy controls in the first cohort, replicated in the second independent cohort, suggested that serum sIFNAR2 levels are a diagnostic biomarker for MS. To evaluate same, ROC curve analysis of the pooled cohorts was carried out for evaluating the precision and discriminating capacity of the diagnostic test. The AUC obtained was of 0.79 (95% area confidence limits=0.74 to 0.85, p<0.001) (FIG. 15B)

The specificity and sensitivity range obtained in this test will depend on the cut-off line established by the observer. The optimum cut-off value for discriminating between MS patients and healthy controls was 1.4, which resulted in a sensitivity (true positive rate) of 80.55% and a specificity (false positive rate) of 70.52%. In this study, sensitivity is defined as the percentage of MS patients correctly identified. This optimum cut-off point gives priority to sensitivity over specificity since the clinical utility of the determination is sIFNAR2 as a screening method for identifying MS patients.

Although the determination of sIFNAR2 in serum, as shown in the examples of the invention, already has a high discriminating powder for a univariate indicator, another additional marker could improve the discriminating capacity of sIFNAR2 and MS diagnosis specificity, as described with other biomarkers. For example, serum sIFNAR2 and C-reactive protein could improve the diagnosis of patients with gastrointestinal cancer and hepatobiliary-pancreatic cancer. Another example is the two-fold increase in the detection of iron deficiency anemia when three parameters were used in combination (ferritin, RsTf, and the RsTf index) instead of ferritin alone.

The sIFNAR2 levels could be added to the panel of other potential laboratory diagnostic biomarkers described in MS such as CSF OCB IgG and/or KFLC (Kappa Free Light Chains) LCR, MRZ reaction (measles-rubella-Zoster Endothecal reaction) or the serum vitamin D.31 levels. These biomarkers have sensitivity and specificity values close to the values obtained with sIFNAR2 and with the advantage that the determination thereof is carried out in serum.

Example 3

The Soluble Isoform of the IFNAR2 Subunit (SIFNAR2) can Modulate IFNβ Activity and Therefore the Associated Immune Response Five patients with high sIFNAR2 levels and five patients with low sIFNAR2 levels have been selected and proinflammatory cytokine profiles have been analyzed starting from peripheral blood mononuclear cells.

Patients with high sIFNAR2 levels showed low TNF-alpha and IFN-gamma levels, whereas patients with low sIFNAR2 levels showed higher TNF-alpha and IFN-gamma levels (FIG. 16).

The increase in sIFNAR2 could be due to an attempt to neutralize the abnormal proinflammatory response occurring in the disease.

Example 4

Evaluation of sIFNAR2 in CIS Patients

In the onset of multiple sclerosis, there is a preclinical phase in which there are lesions, but no symptom manifestations. Suspected presence of the disease starts with the onset of the first clinically isolated syndrome (CIS). These syndromes indicate a suspicion, but not a confirmation of suffering multiple sclerosis. The confirmation of the disease or, as it is clinically called, the change to clinically defined multiple sclerosis (CDMS), occurs when the patient has another clinical syndrome in which spatial dissemination of the lesions (presence of symptoms and signs indicating the existence of two independent lesions in the CNS) and temporal dissemination (two or more episodes of neurological dysfunction) are confirmed.

Some time passed from the onset of a CIS until the diagnosis of the disease (CDMS). Ruling out the disease or diagnosing it after the manifestation of a syndrome is of utmost importance for patients and the clinician. To that end, the serum sIFNAR2 levels of CIS patients were assessed.

Based on the developed ELISA, 43 patients having a CIS were included in the study of which 27 converted to multiple sclerosis.

Figure 12:
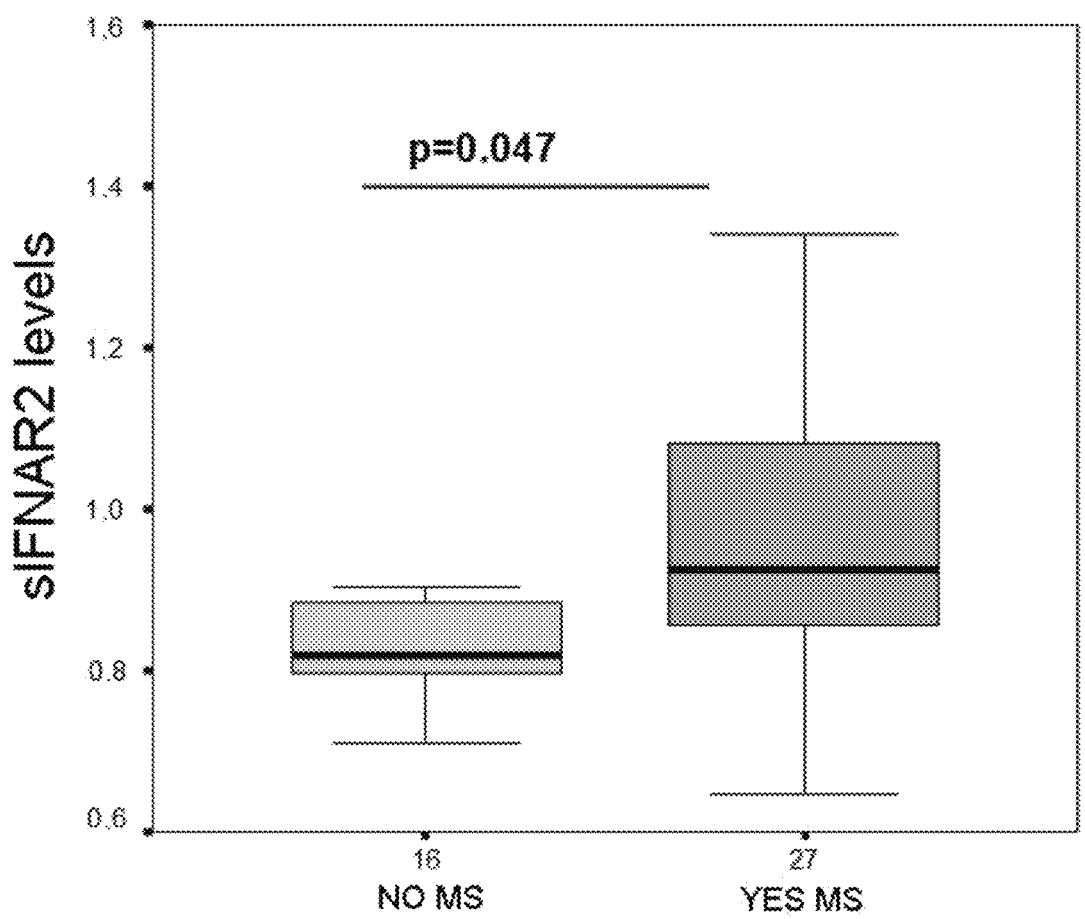
FIG. 12 shows the non-parametric statistical analysis of sIFNAR2 levels in CIS patients who convert or do not convert to sclerosis. NO MS=patients who do not convert to sclerosis. YES MS=patients who convert to defined multiple sclerosis.
Figure 14:
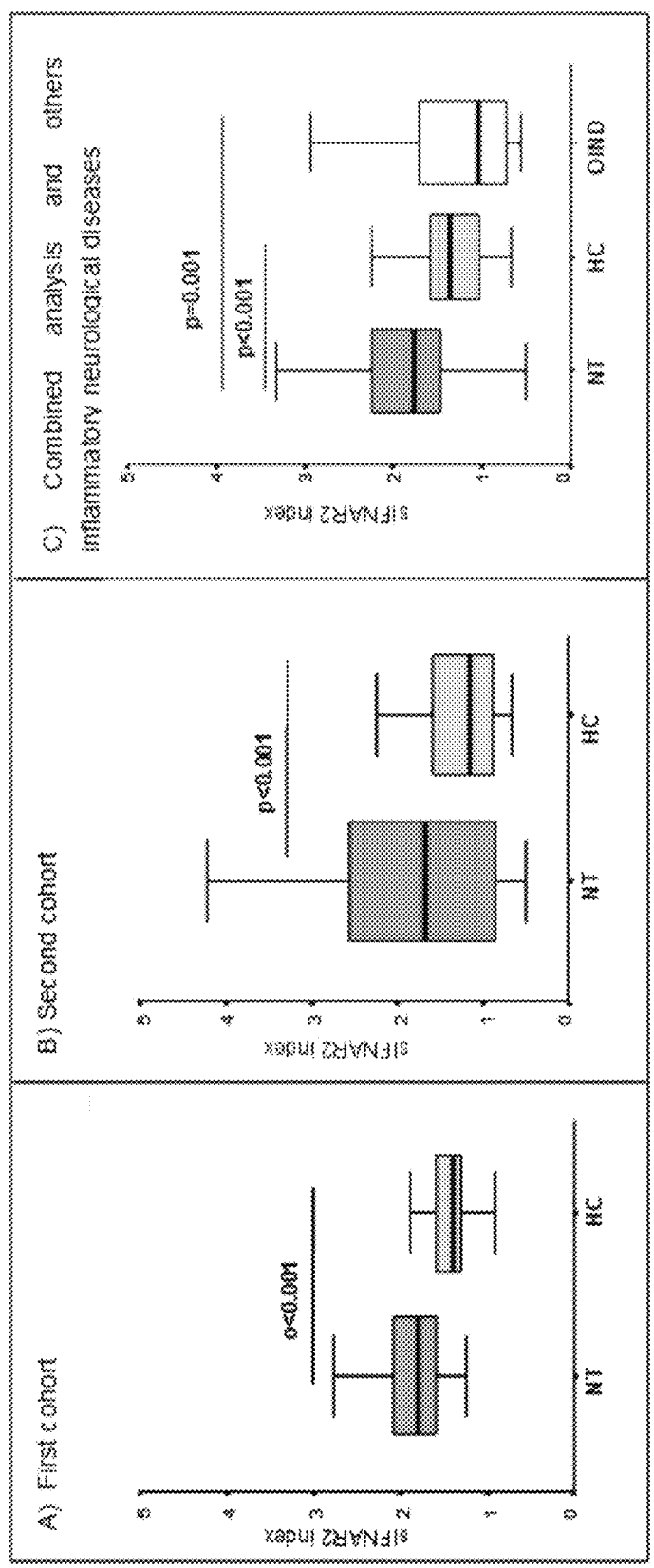
FIG. 14 shows serum sIFNA2R2 levels determined in two independent cohorts of untreated MS patients (NT) and healthy controls (HC) (A and B). The analysis conducted with mixed cohorts and other inflammatory neurological diseases (OIND) (C). The data was analyzed using Kruskal-Wallis one-way analysis of variance test followed by Mann-Whitney U test.

FIG. 12 and Table 9 show that patients who have a CIS and will progress to MS have greater and significant levels with respect to those who will not progress to MS (p=0.047) with respective medians and interquartile ranges.

Table 9. Median and interquartile range of the serum sIFNAR2 values in CIS patients who convert or do not convert to MS

|  | No MS | Yes MS |
|---|---|---|
| N | 16 | 27 |
| Median | 0.82 | 0.92 |
| $P_{25}$-$P_{75}$ | 0.79-0.89 | 0.85-1.08 |

Example 5

Therapeutic Efficacy of Soluble IFNAR2 (sIFNAR2)

To measure the therapeutic efficacy of sIFNAR2 in MS, mice with chronic progressive (CP) experimental autoimmune encephalitis (EAE) were used as animal models. The animal models were divided into four groups with a size of n=5:

| Group | Compound | Size (n) |
|---|---|---|
| Group I | Saline serum (carrier) | n = 5 |
| Group II | IFN-beta (10,000 U = 40 nanograms/mouse) | n = 5 |
| Group III | -sIFNAR2 (40 nanograms/mouse) | n = 5 |
| Group IV | IFN-beta + sIFNAR2 (the same concentration) | n = 5 |

The treatment consisted of the chronic administration of each of the compounds intraperitoneally from day 8 post-immunization (8 dpi) (before the onset of symptoms) and every 3 days until the end of the experiment.

The combined administration of IFN-beta+sol. IFNAR (sIFNAR2) in one and the same animal has been performed by first administering IFNb and administering sIFNAR2 after 15-20 minutes, both also intraperitoneally.

The data is shown as mean±standard error of the mean of the values obtained from 5 animals in each experimental group.

a) Preventive Treatment

The results are shown in FIGS. 17 and 18 and in Tables 15 and 16

TABLE 15

Results of the Newman-Keuls multiple comparison test. Preventive treatment.

| Newman-Keuls multiple comparison test | Mean difference | q | Significant? P < 0.05? | Summary |
|---|---|---|---|---|
| IFN-beta vs saline | −0.1481 | 1.361 | No | ns |
| Chronic soluble IFNAR vs saline | −0.7319 | 6.724 | Yes | *** |
| IFNb + chronic sol. IFNAR vs saline | −0.3548 | 3.26 | Yes | * |
| Chronic soluble IFNAR vs IFN-beta | −0.88 | 8.085 | Yes | +++ |
| IFNb + chronic sol. IFNAR vs IFN-beta | −0.503 | 4.621 | Yes | ++ |
| IFNb + chronic sol. IFNAR vs chronic soluble IFNAR | −0.377 | 3.464 | Yes | * |

T-Test

TABLE 16

Preventive treatment "end-point".

|  | Chronic saline | Chronic IFNb | Chronic sol. IFNAR | IFNb + Chronic sol. IFNAR |
|---|---|---|---|---|
| Incidence of the disease | 5/5 | 5/5 | 5/5 | 5/5 |
| Mortality | 0/5 | 0/5 | 0/5 | 0/5 |
| Day disease onset | 10 ± 0.0 | 11.4 ± 0.8 | 14.4 ± 0.4***++¶ | 11.4 ± 0.7* |
| Maximum Score | 1.9 ± 0.2 | 2.2 ± 0.2 | 1.4 ± 0.1*++ | 1.6 ± 0.2+ |
| Cumulative Score | 37.5 ± 4.4 | 41.5 ± 3.8 | 17.7 ± 1.4**+++¶ | 27.9 ± 4.0+ |

Results

All the therapies administered in a preventive manner, including the saline serum (carrier), modify the normal course of chronic progressive EAE. The outbreak is more moderate and scaled over time, and the chronification of the disease is not as obvious until day 31-32 DPI.

The IFNb administered before the onset of symptoms seems to aggravate the disease, developing a more serious EAE than in animals treated with saline (The maximum score and cumulative score the animals experienced are greater than those treated with the rest of the compounds).

The sIFNAR2 delays the onset of symptoms and, both the maximum score and the cumulative score are considerably lower than those treated with saline. This indicates that the EAE (outbreak) is more moderated in animals treated with sol. IFNAR. However, over time (chronification), the clinical score of the animals is similar to the clinical score of those treated with saline.

Combined Administration: The effects of sIFNAR2 and IFNb counteract one another to a certain extent. Animals with this therapy develop CP-EAE that is more moderate than animals treated with saline and with IFNb alone. Both the maximum score and cumulative score of the animals with this double therapy is lower. Over time (chronification), the clinical score is similar to the clinical score of those treated with saline and with sIFNAR2 as the only therapy.

Conclusions of the Preventive Treatment:

1. The compounds administered in a preventive manner change the clinical course of the chronic progressive EAE model.

2. IFNb does not have any beneficial therapeutic effect on animals with induced CP-EAE, but rather intervenes by aggravating the disease.

3. sIFNAR2 modulates the development of induced CP-EAE: moderates the severity thereof and delays both the onset of the disease and the chronification of clinical symptoms. However, the therapeutic effect seems to be limited over time since, in the chronification of the disease, the neurological deficit of the animals becomes the same as that of animals treated with saline.

4. Combined administration: IFNb and sIFNAR2 interact (in some way) exerting their effects. The results have two readings:

A. sIFNAR2 counteracts the effect of IFNb, moderating the severity of EAE, and making, in the chronification of the disease, the neurological deficit to become the same as the values attained by the animals treated with saline.

B. IFNb counteracts the effect of sIFNAR2, reducing its therapeutic effect, before the chronification of the disease.

b) Clinical Treatment

The treatment consisted of the chronic administration of each of the compounds intraperitoneally after the clinical manifestation of the disease (14 DPI) and every 3 days until the end of the experiment.

Experimental Groups:

| Group | Compound | Size (n) |
|---|---|---|
| Group I | Saline serum (carrier) | n = 5 |
| Group II | IFN-beta (10,000 U = 40 nanograms/mouse) | n = 5 |
| Group III | –sIFNAR2 (40 nanograms/mouse) | n = 5 |
| Group IV | IFN-beta + sIFNAR2 (the same concentration) | n = 5 |

The administration of IFN-beta+sIFNAR2 in one and the same animal has been performed by first administering IFNb and administering sIFNAR2 after 15-20 minutes, both also intraperitoneally.

The data is shown as mean±standard error of the mean of the values obtained from 5 animals in each experimental group. FIGS. 19 and 20 and Tables X and X

TABLE 17

Results of the Newman-Keuls multiple comparison test. Clinical treatment.

| Newman-Keuls multiple comparison test | Mean difference | q | Significant? P < 0.05? | Summary |
|---|---|---|---|---|
| IFN-beta vs saline | −0.4038 | 3.99 | Yes | ** |
| Chronic soluble IFNAR vs saline | −0.4377 | 4.32 | Yes | ** |
| IFNb + chronic sol. IFNAR vs saline | −0.4385 | 4.33 | Yes | * |
| Chronic soluble IFNAR vs IFN-beta | −0.03385 | — | No | ns |
| IFNb + chronic sol. IFNAR vs IFN-beta | −0.03462 | 0.34 | No | ns |
| IFNb + chronic sol. IFNAR vs chronic soluble IFNAR | −0.000769 | — | No | ns |

TABLE 18

Clinical treatment "end-point".

| | Chronic saline | Chronic IFNb | Chronic sol. IFNAR | IFNb + chronic sol. IFNAR |
|---|---|---|---|---|
| Incidence of the disease | 5/5 | 5/5 | 5/5 | 5/5 |
| Mortality | 0/5 | 0/5 | 0/5 | 0/5 |
| Day disease onset | 10.4 ± 0.6 | 10.2 ± 0.4 | 11.0 ± 0.4 | 10.6 ± 0.3 |
| Maximum Score | 2.3 ± 0.4 | 2.1 ± 0.3 | 1.9 ± 0.3 | 1.8 ± 0.3 |
| Cumulative Score | 46.6 ± 10.0 | 36.1 ± 4.7 | 35.2 ± 5.8 | 35.2 ± 3.3 |

Results

The results indicate that:

Chronic progressive EAE is with a normal clinical course as described. The chronification of the disease is obvious from days 17-19 DPI in all the experimental groups.

From the first dose (on day 14 dpi), both IFNb and sIFNAR2, not only when administered as a "single therapy" but also when they are administered as a "combined therapy", reduce the severity of EAE, these animals showing maximum scores and cumulative scores that are much lower than those treated with serum saline.

The group of animals treated with sIFNAR2 alone experience a slight increase in the clinical score at the end of the experiment, approaching values attained by animals treated with saline.

Combined Administration:

IFNb seems to "counteract", to a certain extent, this slight increase in the severity of EAE suffered by sIFNAR2-treated animals at the end of the experiment.

sIFNAR2 does NOT enhance nor counteract the beneficial effect of IFN-beta on the clinical course of EAE (there is no synergy or blocking of the effects between them when administered together; the IFNb+sIFNAR2 curve is practically parallel to that of IFNb alone).

Conclusions:

1. IFNb exerts a beneficial effect on animals with induced CP-EAE by reducing the severity and the neurological deficit of the animals throughout the course of the disease.

2. sIFNAR2 exerts a therapeutic effect similar to that of IFNb. It reduces the severity and the neurological deficit of the animals throughout the course of the disease. Again, the therapeutic effect seems to be limited over time since, in the final chronification stage, the neurological deficit of the animals tends to become the same as that of animals treated with saline.

3. Combined administration: IFNb and soluble IFNAR interact (in some way) exerting their effects:

A) IFNb "enhances" the beneficial effect of soluble IFNAR in the late chronification stage of the disease, preventing the slight increase in the neurological deficit suffered by the animals treated with soluble IFNAR alone.

B) However, sol. IFNAR does NOT enhance not counteract the beneficial effect of IFNb on the clinical course of EAE (there is no synergy of effects when administered together).

FINAL CONCLUSIONS

1. Soluble IFNAR intervenes by modulating chronic progressive EAE, exerting a beneficial effect on the clinical course and the neurological deficit suffered by the animals with induced EAE.

2. sIFNAR2 exerts a therapeutic effect that is greater than that of IFNb as it is administered in a preventive manner. When administered together, both drugs interact counteracting the effects thereof.

3. sIFNAR2 exerts a therapeutic effect similar to that of IFNb when administered in a clinical manner. The mechanism of action of this beneficial effect seems to be more related to modulation of endogenous IFNb than to interaction with exogenous IFNb since, when administered together, the effect is not modified in any manner.

The invention claimed is:

1. A method for treating or ameliorating multiple sclerosis, the method comprising administering to a subject in need thereof a composition comprising:
   (1) a protein comprising the amino acid sequence SEQ ID NO: 2; or
   (2) a recombinant protein produced by a method comprising: (a) integrating an insert with the nucleotide sequence SEQ ID NO. 1 in an expression vector; (b) transforming a host with the expression vector of step (a); (c) inducing the expression of the recombinant protein; (d) extracting the recombinant protein; and optionally (e) purifying the recombinant protein; or
   (3) a protein that is a soluble isoform of interferon alpha and beta receptor subunit 2 (IFNAR2.3);
   such that said multiple sclerosis is treated or ameliorated.

2. The method of claim 1, wherein the protein in (1), the recombinant protein in (2) or the protein IFNAR2.3 in (3) is administered in combination with interferon β (INFβ).

3. The method of claim 1, wherein treating or ameliorating multiple sclerosis comprises delaying onset of multiple sclerosis.

4. The method of claim 1, wherein treating or ameliorating multiple sclerosis comprises delaying the onset of clinical symptoms of multiple sclerosis.

5. The method of claim 1, wherein treating or ameliorating multiple sclerosis comprises moderating severity of multiple sclerosis.

6. The method of claim 1, wherein the subject has a clinically isolated syndrome (CIS).

* * * * *

SEQUENCE LISTING

<160> NUMBER OF SEQ ID NOS: 6

<210> SEQ ID NO 1
<211> LENGTH: 2479
<212> TYPE: DNA
<213> ORGANISM: Artificial Sequence
<220> FEATURE:
<223> OTHER INFORMATION: nucleotidic sequence coding for a IFNAR2.3

<400> SEQUENCE: 1

| | | | | |
|---|---|---|---|---|
| agatgtaaaa | gtcaagagaa | gactctaaaa | atagcaaaga | tgcttttgag ccagaatgcc | 60 |
| ttcatcttca | gatcacttaa | tttggttctc | atggtgtata | tcagcctcgt gtttggtatt | 120 |
| tcatatgatt | cgcctgatta | cacagatgaa | tcttgcactt | tcaagatatc attgcgaaat | 180 |
| ttccggtcca | tcttatcatg | ggaattaaaa | aaccactcca | ttgtaccaac tcactataca | 240 |
| ttgctgtata | caatcatgag | taaaccagaa | gatttgaagg | tggttaagaa ctgtgcaaat | 300 |
| accacaagat | catttgtga | cctcacagat | gagtggagaa | gcacacacga ggcctatgtc | 360 |
| accgtcctag | aaggattcag | cgggaacaca | acgttgttca | gttgctcaca caatttctgg | 420 |
| ctggccatag | acatgtcttt | tgaaccacca | gagtttgaga | ttgttggttt taccaaccac | 480 |
| attaatgtga | tggtgaaatt | tccatctatt | gttgaggaag | aattacagtt tgatttatct | 540 |
| ctcgtcattg | aagaacagtc | agagggaatt | gttaagaagc | ataaacccga aataaaagga | 600 |
| aacatgagtg | gaaatttcac | ctatatcatt | gacaagttaa | ttccaaacac gaactactgt | 660 |
| gtatctgttt | atttagagca | cagtgatgag | caagcagtaa | taaagtctcc cttaaaatgc | 720 |
| accctccttc | cacctggcca | ggaatcagaa | ttttcataac | tttttagcct ggccatttcc | 780 |
| taacctgcca | ccgttggaag | ccatggatat | ggtggaggtc | atttacatca acagaaagaa | 840 |
| gaaagtgtgg | gattataatt | atgatgatga | aagtgatagc | gatactgagg cagcgcccag | 900 |
| gacaagtggc | ggtggctata | ccatgcatgg | actgactgtc | aggcctctgg gtcaggcctc | 960 |
| tgccacctct | acagaatccc | agttgataga | cccggagtcc | gaggaggagc ctgacctgcc | 1020 |
| tgaggttgat | gtggagctcc | ccacgatgcc | aaaggacagc | cctcagcagt tggaactctt | 1080 |
| gagtgggccc | tgtgagagga | gaaagagtcc | actccaggac | ccttttcccg aagaggacta | 1140 |
| cagctccacg | gaggggtctg | ggggcagaat | taccttcaat | gtggacttaa actctgtgtt | 1200 |
| tttgagagtt | cttgatgacg | aggacagtga | cgacttagaa | gcccctctga tgctatcgtc | 1260 |
| tcatctggaa | gagatggttg | acccagagga | tcctgataat | gtgcaatcaa accatttgct | 1320 |
| ggccagcggg | gaagggacac | agccaacctt | tcccagcccc | tcttcagagg gcctgtggtc | 1380 |
| cgaagatgct | ccatctgatc | aaagtgacac | ttctgagtca | gatgttgacc ttgggggatgg | 1440 |
| ttatataatg | agatgactcc | aaaactattg | aatgaacttg | acagacaag cacctacagg | 1500 |
| gttctttgtc | tctgcatcct | aacttgctgc | cttatcgtct | gcaagtgttc tccaagggaa | 1560 |
| ggaggaggaa | actgtggtgt | tcctttcttc | caggtgacat | cacctatgca cattcccagt | 1620 |
| atggggacca | tagtatcatt | cagtgcattg | tttacatatt | caaagtggtg cactttgaag | 1680 |
| gaagcacatg | tgcacctttc | ctttacacta | atgcacttag | gatgtttctg catcatgtct | 1740 |
| accagggagc | agggttcccc | acagtttcag | aggtggtcca | ggaccctatg atatttctct | 1800 |
| tctttcgttc | tttttttttt | tttttgaga | cagagtctcg | ttctgtcgcc caagctggag | 1860 |
| cgcaatggtg | tgatcttggc | tcactgcaac | atccgcctcc | cgggttcagg tgattctcct | 1920 |
| gcctcagcct | cccctcgcaag | tagctgggat | tacaggcgcc | tgccaccatg cctagcaaat | 1980 |
| ttttgtatttt | ttagtggaga | caggatttta | ccatgttggc | caggctggtc tcgaactcct | 2040 |

-continued

```
gacctcaagt gatctgccct cctcagcctc gtaaagtgct gggattacag gggtgagccg      2100
ctgtgcctgg ctggccctgt gatatttctg tgaaataaat tgggccaggg tgggagcagg      2160
gaaagaaaag gaaatagta gcaagagctg caaagcaggc aggaagggag gaggagagcc       2220
aggtgagcag tggagagaag gggggccctg cacaaggaaa cagggaagag ccatcgaagt      2280
ttcagtcggt gagccttggg cacctcaccc atgtcacatc ctgtctcctg caattggaat      2340
tccaccttgt ccagccctcc ccagttaaag tggggaagac agactttagg atcacgtgtg      2400
tgactaatac agaaaggaaa catggcgtcg gggagaggga taaaacctga atgccatatt      2460
ttaagttaaa aaaaaaaa                                                    2479
```

<210> SEQ ID NO 2
<211> LENGTH: 239
<212> TYPE: PRT
<213> ORGANISM: Artificial Sequence
<220> FEATURE:
<223> OTHER INFORMATION: aminoacidic sequence IFNAR2.3

<400> SEQUENCE: 2

```
Met Leu Leu Ser Gln Asn Ala Phe Ile Phe Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
        195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Phe Ser
225                 230                 235
```

<210> SEQ ID NO 3
<211> LENGTH: 331
<212> TYPE: PRT
<213> ORGANISM: Artificial Sequence
<220> FEATURE:
<223> OTHER INFORMATION: Aminoacidic sequence of the capture antibody

<400> SEQUENCE: 3

```
Met Leu Leu Ser Gln Asn Ala Phe Ile Val Arg Ser Leu Asn Leu Val
1               5                   10                  15

Leu Met Val Tyr Ile Ser Leu Val Phe Gly Ile Ser Tyr Asp Ser Pro
            20                  25                  30

Asp Tyr Thr Asp Glu Ser Cys Thr Phe Lys Ile Ser Leu Arg Asn Phe
        35                  40                  45

Arg Ser Ile Leu Ser Trp Glu Leu Lys Asn His Ser Ile Val Pro Thr
    50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
            115                 120                 125

Ala Ile Asp Met Ser Phe Glu Pro Pro Glu Phe Glu Ile Val Gly Phe
130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
        195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Ser Ala Glu
225                 230                 235                 240

Ser Ala Lys Ile Gly Gly Ile Ile Thr Val Phe Leu Ile Ala Leu Val
                245                 250                 255

Leu Thr Ser Thr Ile Val Thr Leu Lys Trp Ile Gly Tyr Ile Cys Leu
            260                 265                 270

Arg Asn Ser Leu Pro Lys Val Leu Arg Gln Gly Leu Thr Lys Gly Trp
        275                 280                 285

Asn Ala Val Ala Ile His Arg Cys Ser His Asn Ala Leu Gln Ser Glu
    290                 295                 300

Thr Pro Glu Leu Lys Gln Ser Ser Cys Leu Ser Phe Pro Ser Ser Trp
305                 310                 315                 320

Asp Tyr Lys Arg Ala Ser Leu Cys Pro Ser Asp
                325                 330
```

<210> SEQ ID NO 4
<211> LENGTH: 331
<212> TYPE: PRT
<213> ORGANISM: Artificial Sequence
<220> FEATURE:
<223> OTHER INFORMATION: Aminoacidic sequence of the detection antibody

<400> SEQUENCE: 4

```
Met Leu Leu Ser Gln Asn Ala Phe Ile Val Arg Ser Leu Asn Leu Val
1               5                   10                  15
```

Leu Met Val Tyr Ile Ser Leu Val Phe Gly Ile Ser Tyr Asp Ser Pro
                20                  25                  30

Asp Tyr Thr Asp Glu Ser Cys Thr Phe Lys Ile Ser Leu Arg Asn Phe
            35                  40                  45

Arg Ser Ile Leu Ser Trp Glu Leu Lys Asn His Ser Ile Val Pro Thr
50                  55                  60

His Tyr Thr Leu Leu Tyr Thr Ile Met Ser Lys Pro Glu Asp Leu Lys
65                  70                  75                  80

Val Val Lys Asn Cys Ala Asn Thr Thr Arg Ser Phe Cys Asp Leu Thr
                85                  90                  95

Asp Glu Trp Arg Ser Thr His Glu Ala Tyr Val Thr Val Leu Glu Gly
            100                 105                 110

Phe Ser Gly Asn Thr Thr Leu Phe Ser Cys Ser His Asn Phe Trp Leu
        115                 120                 125

Ala Ile Asp Met Ser Phe Glu Pro Pro Glu Phe Glu Ile Val Gly Phe
    130                 135                 140

Thr Asn His Ile Asn Val Met Val Lys Phe Pro Ser Ile Val Glu Glu
145                 150                 155                 160

Glu Leu Gln Phe Asp Leu Ser Leu Val Ile Glu Gln Ser Glu Gly
                165                 170                 175

Ile Val Lys Lys His Lys Pro Glu Ile Lys Gly Asn Met Ser Gly Asn
            180                 185                 190

Phe Thr Tyr Ile Ile Asp Lys Leu Ile Pro Asn Thr Asn Tyr Cys Val
        195                 200                 205

Ser Val Tyr Leu Glu His Ser Asp Glu Gln Ala Val Ile Lys Ser Pro
    210                 215                 220

Leu Lys Cys Thr Leu Leu Pro Pro Gly Gln Glu Ser Glu Ser Ala Glu
225                 230                 235                 240

Ser Ala Lys Ile Gly Gly Ile Ile Thr Val Phe Leu Ile Ala Leu Val
                245                 250                 255

Leu Thr Ser Thr Ile Val Thr Leu Lys Trp Ile Gly Tyr Ile Cys Leu
            260                 265                 270

Arg Asn Ser Leu Pro Lys Val Leu Arg Gln Gly Leu Thr Lys Gly Trp
        275                 280                 285

Asn Ala Val Ala Ile His Arg Cys Ser His Asn Ala Leu Gln Ser Glu
    290                 295                 300

Thr Pro Glu Leu Lys Gln Ser Ser Cys Leu Ser Phe Pro Ser Ser Trp
305                 310                 315                 320

Asp Tyr Lys Arg Ala Ser Leu Cys Pro Ser Asp
                325                 330

<210> SEQ ID NO 5
<211> LENGTH: 46
<212> TYPE: DNA
<213> ORGANISM: Artificial Sequence
<220> FEATURE:
<223> OTHER INFORMATION: forward primer

<400> SEQUENCE: 5
taaggcctct gtcgacattt catatgattc gcctgattac acgatg         46

<210> SEQ ID NO 6
<211> LENGTH: 45
<212> TYPE: DNA
<213> ORGANISM: Artificial Sequence
<220> FEATURE:
<223> OTHER INFORMATION: Reverse primer sequence -continued

```
<400> SEQUENCE: 6
cagaattcgc aagctttgaa aattctgatt cctggccagg tggaa              45
```